United States Patent [19]

Itoh et al.

[11] 4,112,746
[45] Sep. 12, 1978

[54] OPTO-ELECTRONIC TENSILE TESTING SYSTEM

[75] Inventors: Hiroyuki Itoh, Kawasaki; Kenhachi Mitsuhashi, Hiratsuka; Hiromitsu Akashi, Ise, all of Japan

[73] Assignees: The Yokohama Rubber Co., Ltd.; Fuji Telecasting Co., Ltd., both of Japan

[21] Appl. No.: 782,492

[22] Filed: Mar. 29, 1977

[30] Foreign Application Priority Data

Apr. 2, 1976 [JP] Japan .................................. 51-37541
Jun. 10, 1976 [JP] Japan .................................. 51-68058
Oct. 6, 1976 [JP] Japan .................................. 51-120180
Oct. 29, 1976 [JP] Japan .................................. 51-131088
Jan. 20, 1977 [JP] Japan .................................. 52-5214

[51] Int. Cl.$^2$ ............................................. G01N 3/08
[52] U.S. Cl. ............................................................ 73/95
[58] Field of Search ............................. 73/88 A, 95, 90

[56] References Cited
U.S. PATENT DOCUMENTS

3,592,545  7/1971  Paine .................................... 73/95 X
4,031,746  6/1977  Furuta et al. ........................... 73/95

*Primary Examiner*—Jerry W. Myracle
*Attorney, Agent, or Firm*—Robert E. Burns; Emmanuel J. Lobato; Bruce L. Adams

[57] ABSTRACT

A tensile testing system for use with a specimen of rubber or other material having a test region defined on its reduced midportion by a marking or markings of, for example, higher lightness than the other specimen surface. The system comprises a scanning device for repeatedly translating the optical characteristics of the specimen or specimens into an electrical signal as the specimen or specimens are subjected to increasing tensile stress, and a gate circuit for deriving from the output signal of the scanning device its portions corresponding to the test region or regions. The varying length of the test region or regions can be represented either by pulse durations or by pulse numbers. The scanning device can be either an "area scanner" such as a television camera or a "line scanner" such as a solid-state line image sensor. Various embodiments are disclosed.

25 Claims, 37 Drawing Figures

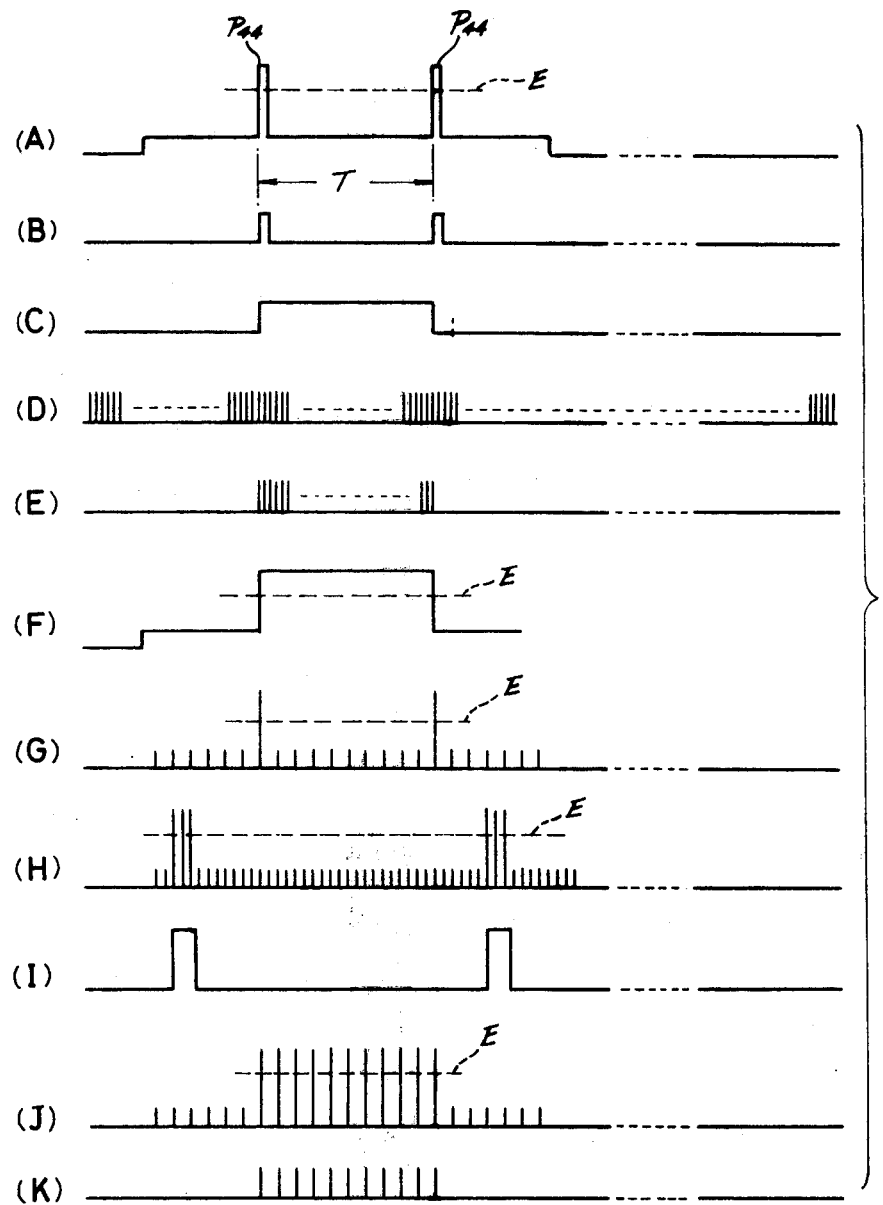

FIG. 27
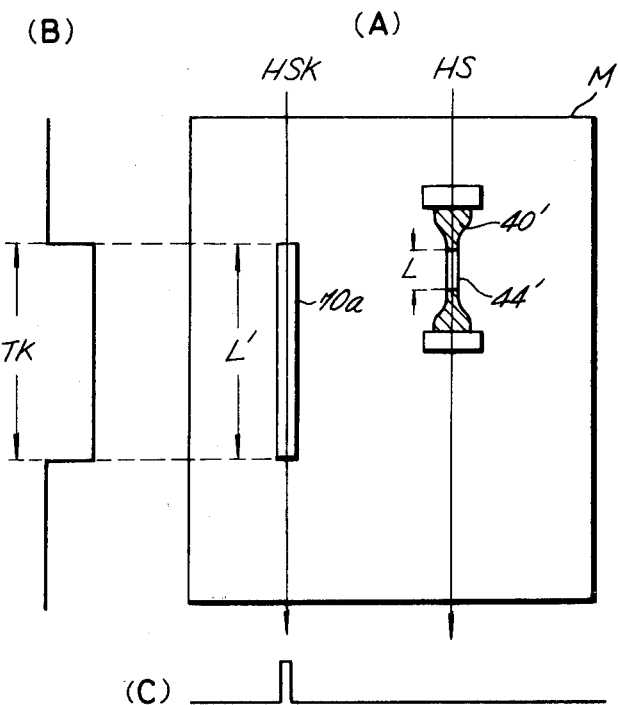
FIG. 28A   FIG. 28B
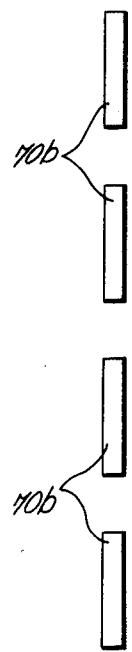
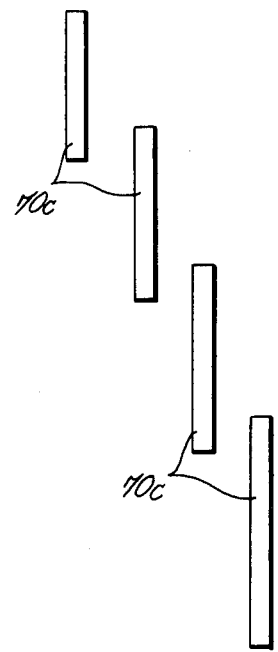

OPTO-ELECTRONIC TENSILE TESTING SYSTEM

BACKGROUND OF THE INVENTION

1. Field of the Invention

Our invention relates to tensile testing systems and is directed more specifically to a system for opto-electronically testing the stress-strain properties of materials under tension. The materials suitable to be tested by the system of our invention includes, for example, rubbers, fibers, and plastics.

2. Description of the Prior Art

In the tensile testing of the above listed materials, the ends of a specimen tend to slip away from the pair of chucks or gripping means of the testing machine as the tensile stress on the specimen increases. The distance between the chucks, therefore, does not provide the true measure of the specimen elongation. The usual practice heretofore adopted to overcome this problem has been to mark the specimen with a pair of longitudinally spaced lines and to visually measure the spacing therebetween with the aid of a scale.

Such visual or manual measurements, however, have poor reproducibility and are subject to significant variation from individual to individual. Furthermore, where the tensile moduli (i.e., the quotient of the tensile stress divided by the cross sectional area of the specimen) at, for example, 100, 200 and 300% specimen elongations are required, these elongations must be ascertained visually even though provision may be made for automatic measurement of the stresses on the specimen. The manual measurement of specimen elongation has thus been highly troublesome, time-consuming, and has required an undue amount of manpower.

We are aware of several instruments already suggested for automatic measurement of specimen elongation, but these prior art instruments are unsatisfactory for one or other of the following reasons. In some instances some special appendages must be attached to specimens, such appendages including armatures for detection of magnetism or levers for actuation of differential transformers. According to another known system wherein photoelectric elements are employed for detecting and tracking the markings on a specimen, detector means must be disposed in the close proximity of the specimen, and a drive mechanism is also required for tracking the specimen markings.

In both cases considerable difficulties are encountered as to the mounting and demounting of specimens on and from the testing machine. With these prior art systems, moreover, positional adjustment of the armatures and the photoelectric elements must be made in preparation for actual testing.

SUMMARY OF THE INVENTION

It is, accordingly, an object of our invention to provide an improved tensile testing system for accurate, automatic measurement of stress-strain properties of materials in tension.

Another object of our invention is to provide a tensile testing system which necessitates no troublesome preparation of specimens and which permits ready mounting and demounting of specimens on and from the testing machine.

A further object of our invention is to provide a tensile testing system capable of simultaneously and individually testing a plurality of specimens.

A still further object of our invention is to provide an opto-electronic tensile testing system whereby desired data can be obtained accurately without being affected by ambient optical conditions of a specimen being tested or by some undesired optical characteristics of the specimen itself.

The tensile testing system in accordance with our invention is contemplated for use with a specimen having a test region defined thereon by a marking or markings having a different optical characteristic from the other surface of the specimen. Stated in its perhaps simplest form, the tensile testing system comprises a scanning device (as hereinafter defined) for translating the optical characteristics of the specimen into an electrical signal, with the device being adapted to scan the specimen repeatedly as same is subjected to increasing longitudinal pulling stress, and circuit means for deriving from the output signal of the scanning device its portions representing the varying length of the test retion of the specimen.

The marking or markings on the specimen must differ from the other specimen surface in any of such optical properties as lightness, brightness, hue, saturation, etc., in order that the marked and the unmarked surface portions of the specimen may cause corresponding differences in the output magnitude of the scanning device. This objective can be attained, for example, by coating the entire test region, its boundaries, or portions other than the test region, of the specimen with a paint of higher or lower lightness than the specimen surface.

The tensile testing system of our invention presupposes the use of a testing machine of the type whereby the specimen of the foregoing character is gripped at both ends and is subjected to longitudinal pulling stress as the pair of specimen gripping means of the machine move relatively away from each other. Such a testing machine should be adapted for use with a load cell or a strain gage.

The term "scanning device" is used in the broad sense herein and in the claims appended hereto; it can be either an "area scanner" such as a television camera or a solid-state "area" image sensor capable of scanning a two-dimensional scene, or a "line scanner" such as a "line scanning" pickup tube or a solid-state "line" image sensor capable of scanning an object along a single line. A combination of laser scaner and light receptor is an additional example of the scanning device. If desired, a "line scanner" may be used as "area scanner", by repeatedly scanning supplementarily in the direction at right angles with its principal scanning line, at a higher frequency than that of the scanning along the principal line. With a "line scanner" employed as the scanning device, the specimen is of course scanned along a line extending in its longitudinal direction.

In a preferred embodiment of our invention, the portions derived as aforesaid from the output signal of the scanning device are utilized to produce gate pulses ("test region signal") the durations of which represent the increasing length of the test region of the specimen. These gate pulses are used for gating clock pulses of a prescribed recurrence rate, and the gated clock pulses are counted by a binary or a binary coded decimal counter during each "area" or "line" scanning operation.

Let it be supposed, for example, that a dark-surfaced specimen having a test region defined thereon by a marking or markings of high lightness is mounted against a dark background on a desired testing machine.

Each time the scanning device scans the specimen to produce an electrical signal representing the optical characteristics of the specimen in its longitudinal direction, the signal will include a higher level portion or portions corresponding to the marking or markings on the specimen. This output signal of the scanning device is processed to provide the aforementioned gate pulse the duration of which represents the length of the test region.

Thus, as the specimen is scanned repeatedly with the increase in the pulling stress exerted thereon, the duration of the successive gate pulses will increase in step with the elongation of the test region. The increasing length of the test region can be ascertained from the count made by the counter during each scanning operation, until fracture occurs. The successive counts of the counter may be stored, recorded, and/or displayed by any suitable equipment.

The counts made by the counter can be obtained in the form of a binary or a binary coded decimal signal, so that if desired, the signal may be delivered to an arithmetic processing circuit for computation of the actual length of the test region. It is also possible to manually calculate the test region length from the counts of the counter. In this latter case the counter counts may be either displayed along with the corresponding stresses, recorded on paper, or stored in a memory.

For conversion of the counts of the counter into a convenient unit of length, the counter count must be known which corresponds to the initial length of the test region, that is, the test region length before the specimen is stressed. Preferably, the recurrence rate of the clock pulses may be so determined that there will be one-to-one correspondence between each count of the counter and the actual length of the test region as expressed in a desired unit. For example, the counter count may be 20 when the test region length is 20 millimeters. It should be noted, however, that the aforesaid test region signal can itself be adopted for indication of the test region length.

The tensile testing system of our invention is readily adaptable for simultaneous testing of a plurality of specimens mounted on a common testing machine in side-by-side relationship. The scanning device in this case should be an "area scanner", and its output signal may be divided into portions corresponding to the respective specimens. The divided signal portions can each be processed in the same fashion as in the above described case of the testing of a single specimen.

In order to accurately ascertain the length of the test region of a specimen without being affected by foreign matter that may exist in its neighborhood, gate circuit means can be employed for deriving from the output signal of the scanning device its portions corresponding to the marking or markings on the specimen. The gate signals used for this purpose are herein termed "boundary signals".

If the scanning device in use is a "line scanner", there is used a "longitudinal boundary" gate signal for establishing the boundaries of measurement in the longitudinal direction of the specimen. If the scanning device in use is an "area scanner", then there are used the longitudinal boundary gate signal and a "transverse boundary" gate signal for establishing the transverse boundaries of measurement on both sides of the specimen. These boundary signals can be easily produced by utilizing a signal or signals delivered from a reference signal generator to the scanning device for driving the latter, or by utilziing the output signal of the scanning device itself.

A specimen of rubber, in particular, usually ruptures after several hundred percent elongation, so that each pulse duration of the longitudinal boundary signal should preferably be increased in step with the elongation of the test region. Moreover, since the test region undergoes gradual displacement from its initial position along with its elongation, the leading and the trailing edges of the successive longitudinal boundary pulses should be correspondingly shifted in time.

The above and other objects, features and advantages of our invention and the manner of attaining them will become more apparent, and the invention itself will best be understood, from the following description of several preferred embodiments, which is to be read in connection with the accompanying drawings.

BRIEF DESCRIPTION OF THE DRAWINGS

FIG. 3 is a graphic representation of various waveforms useful in explaining the operation of the tensile testing system of FIG. 2;

FIG. 27 is a graphic representation of waveforms useful in explaining the operation of the means of FIG. 26, with the waveforms being plotted in relation to a reference length member and a specimen being tested;

FIG. 28A shows an example of arrangement of a plurality of reference length members;

FIG. 28B shows another example of arrangement of the reference length members;

DESCRIPTION OF THE PREFERRED EMBODIMENTS

Figure 1A:
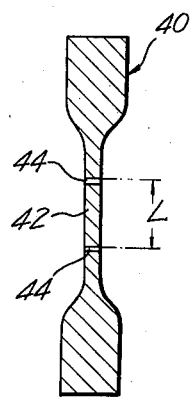
FIG. 1A shows an example of specimen for use with the tensile testing system of our invention.
Figure 1B:
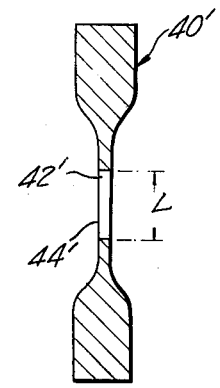
FIG. 1B shows another example of specimen for use with the tensile testing system of our invention.

Referring now in detail to the several embodiments herein chosen for the purpose of illustrating our invention, it will be seen from FIGS. 1A and 1B that both types of specimens 40 and 40' to be subjected to tensile tests in accordance with the invention have a reduced midportion. In the specimen 40 of FIG. 1A the central region 42 of its reduced midportion is marked out with a pair of parallel, longitudinally spaced lines 44 which are of, for example, higher lightness than the other surface of the specimen. The specimen 40' of FIG. 1B, on the other hand, has the central region 42' of its reduced midportion completely covered with a marking 44' of, for example, higher lightness than the other surface of the specimen. The thus-marked regions 42 and 42' of the specimens 40 and 40' are referred to herein and in the appended claims as the "test regions".

Each cf the specimens 40 and 40' of the foregoing configuration is intended to be gripped at its shouldered ends by a pair of chucks or gripping means (seen at 64 in FIG. 4) of a suitable testing machine, such as of the conventional Schopper type, and to be thereby subjected to increasing longitudinal pulling stress as the pair of gripping means move relatively away from each other. In the following description of the several embodiments the markings 44 and 44' and the specimen gripping means are understood to be of higher lightness than the unmarked parts of the specimen surfaces and the background.

Figure 2:
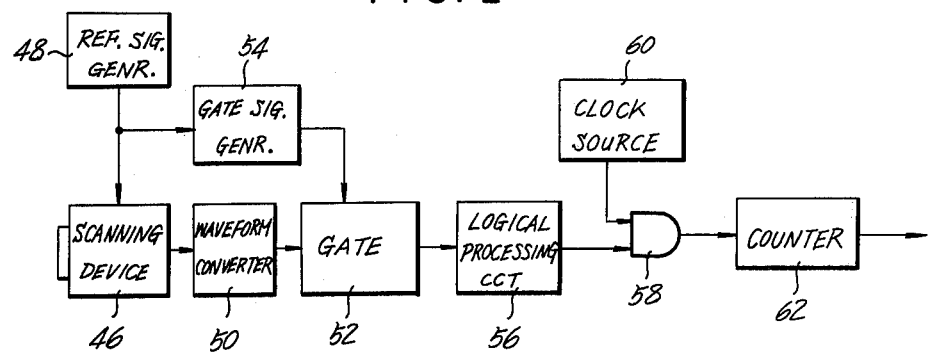
FIG. 2 is a block diagram of the tensile testing system embodying our invention.

As schematically depicted in FIG. 2, the tensile testing system in accordance with our invention includes a scanning device 46 to which is connected the output of a reference signal generator 48 for driving the scanning device or for controlling its scanning operation. During the tensile testing of the specimen 40 or 40', the scanning device 46 repeatedly scans the specimen (or its optically reproduced image) and produces an electrical signal representing the optical characteristics of the specimen in its longitudinal direction. The output of the scanning device 46 is connected to a waveform converter 50.

If the specimen 40 of FIG. 1A is to be tested, for example, the scanning device 46 must be so positioned with respect to the specimen, which is mounted in position on the testing machine, that the output signal thereof may include portions corresponding to the pair of higher lightness lines 44 bounding the test region 42 of the specimen, in spite of the increasing distance therebetween. If the scanning device in use is of the "line scanning" type such as a pickup tube, for example, then there will be produced therefrom an output signal graphically represented at A in FIG. 3 each time the specimen is scanned in its longitudinal direction. In the waveform given at A in FIG. 3, of course, the two high level portions or pulses P44 represent the pair of higher lightness lines 44 on the specimen 40.

The waveform converter 50 can in practice be a shaping circuit such as a known Schmitt circuit or amplitude comparator. This waveform converter derives from the scanning device output signal only its portions lying above a prescribed amplitude level E, indicated at A in FIG. 3, and thus converts the scanning device output signal into a digital signal. The output of the waveform converter 50 is connected to a gate circuit 52.

Since the output signal of the scanning device 46 may include high level portions other than the desired portions P44, such as those representing the specimen gripping means of the testing machine, the gate circuit 52 is intended to eliminate the corresponding undesired high level portions that may be contained in the digital output from the waveform converter 50. To this end there is connected between the reference signal generator 48 and the gate circuit 52 a "boundary" gate signal generator 54 which produces, by utilizing a reference signal or signals generated by the generator 48, a boundary gate signal or signals representative of boundaries for the measurement of the test region of the specimen, as will more fully appear as the description proceeds. Supplied with the boundary gate signal or signals from the generator 54, the gate circuit 52 permits the passage therethrough of only those portions of the waveform converter output signal which correspond to the test region and to its immediate vicinity.

The consequent output signal of the gate circuit 52 is represented at B in FIG. 3. It will be apparent that the two pulses of the gate circuit output signal correspond to the two high level portions P44 of the scanning device output signal given at A in FIG. 3, which in turn represent the pair of higher lightness lines 44 bounding the test region 42 of the specimen.

The output of the gate circuit 52 is connected to a logical processing circuit 56 which in this particular embodiment can take the form of a trigger flip-flop. By this flip-flop is the output signal of the gate circuit 52 converted into a "test region" signal represented at C in FIG. 3. It will be seen that this test region signal includes a relatively long duration pulse whose duration corresponds to the time T from the leading edge of the first gate circuit output pulse to that of the next pulse, and therefore to the length of the test region of the specimen.

Connected to the output of the logical processing circuit 56 is one of the inputs of a two-input AND gate 58, the other input of which is connected to a clock 60. The logical processing circuit 56 delivers the test region signal to the AND gate 58 as a gate signal, whereas the clock 60 delivers thereto the accurately timed clock pulses represented at D in FIG. 3. The AND gate 58 operates in the well known manner to permit the passage therethrough of only those of the clock pulses which are supplied thereto while the test region signal being also supplied thereto is of high level.

The output pulses of the AND gate 58, represented at E in FIG. 3, are delivered to, and counted by, a counter 62 which can be either of the binary type or of the binary coded decimal type. This counter is adapted to be cleared upon completion of each scanning operation.

As will be evident from the foregoing, the time interval between the two pulses P44 included in the output from the scanning device 46 corresponds to the length of time during which the test region 42 of the specimen 40 is being scanned. Of course, this time interval increases in step with the increase in the length L of the test region as increasing tensile stress is exerted on the specimen. Thus, in accordance with our invention, the increasing length of the test region of the specimen can be determined from the counts provided by the counter 62 upon completion of successive scanning operations.

If the test specimen is of the type designated 40' in FIG. 1B, the scanning device 46 will produce, each time it scans the specimen in its longitudinal direction, an output signal which as represented at F in FIG. 3, has a single high level portion or pulse corresponding to the entire test region 42' of the specimen covered with the higher lightness marking 44'. The waveform converter 50 extracts from this scanning device output signal only its portion lying above the prescribed level E, producing an output signal identical with that shown at C in FIG. 3. This waveform converter output signal is also delivered to the gate circuit 52 for the above described purposes, and the consequent output signal of the gate circuit can be delivered directly to the AND gate 58 as the mentioned test region signal. It is thus seen that the logical processing circuit 56 can be omitted in the case where a "line scanning" pickup tube is employed in conjunction with the specimen 40' of FIG. 1B.

The tensile testing system in accordance with our invention permits the use of a television camera or like "area scanner" as the scanning device 46, as mentioned previously. If a television camera is employed for scanning the specimen 40 of FIG. 1A along a prescribed pattern or raster of parallel lines extending transversely of the specimen, that is, in a direction at right angles with the direction in which the specimen is tensioned, then the output signal thereof will be as represented at G in FIG. 3. In this case, too, the waveform converter 50 extracts from the television camera output signal only its portions above the prescribed level E, producing an output signal similar to that represented at B in FIG. 3.

With the progress of the tensile testing of the specimen 40, however, each of the pair of higher lightness lines 44 bounding its test region 42 gradually increases in width, until each line 44 spans two or more of the transverse scanning lines. Thereupon the television camera will produce an output signal represented at H in FIG. 3, wherein each higher lightness line 44 on the specimen is represented by a train of two or more pulses.

In this case, therefore, there may be incorporated in the logical processing circuit 56 a sampling and holding circuit or a retriggerable monostable multivibrator with a time constant slightly longer than each transverse scanning period of the television camera. Thus, delivered to the logical processing circuit 56 via the waveform converter 50, the television camera output signal given at H in FIG. 3 can be converted into a signal represented at I in FIG. 3, wherein each pulse represents one of the higher lightness lines on the specimen 40. This signal is further delivered to the trigger flip-flop to obtain the test region signal represented at C in FIG. 3.

If a television camera or like "area scanner" is employed for scanning the specimen 40' of FIG. 1B, also along a prescribed pattern of parallel lines extending transversely of the specimen, then the output signal thereof will have the waveform given at J in FIG. 3, representing the higher lightness test region 42' of the specimen by a train of high level pulses. Delivered to the waveform converter 50, the output signal of the camera is converted into the waveform represented at K in FIG. 3. This waveform converter output signal is delivered to the gate circuit 52, for the purposes set forth previously, and thence directly to the counter 62.

It will thus be seen that the increasing length of the higher lightness test region 42' of the specimen 40' can be determined from the correspondingly increasing number of the scanning lines encompassed within the test region. It will also be apparent that in this case, the tensile testing system of our invention can dispense with the logical processing circuit 56, the AND gate 58, and the clock 60. Alternatively, the output signal of the waveform converter 50 may be delivered to the aforesaid sampling and holding circuit or retriggerable monostable multivibrator in the logical processing circuit 56, in order to obtain the test region signal similar to that given at C in FIG. 3. This signal can then be delivered to the AND gate 58 for gating the clock pulses being also supplied thereto.

The tensile testing system in accordance with our invention further permits the use of a solid-state "area" image sensor or "line" image sensor as the scanning device 46. In such an image sensor, as is well known, clock pulses are applied to an array or series of photoelectric elements to cause selective conduction thereof, with the result that the output signal of the image sensor contains pulses equal in number to those of the elements which correspond to the higher lightness surfaces of the area or line being scanned. In this case, too, therefore, a sampling and holding circuit or retriggerable monostable multivibrator may be used in the logical processing circuit 56 or, alternatively, the output signal of the gate circuit 52 may be delivered directly to the counter 62.

Although in the tensile testing system of FIG. 1 the digital gate circuit 52 is provided in the succeeding stage of the waveform converter 50 for elimination of undesired high level portions or pulses that may be contained in the digital output of the latter, an analog gate circuit may be employed as desired for the same purpose. Such an analog gate circuit preceds the waveform converter 50.

Figure 4:
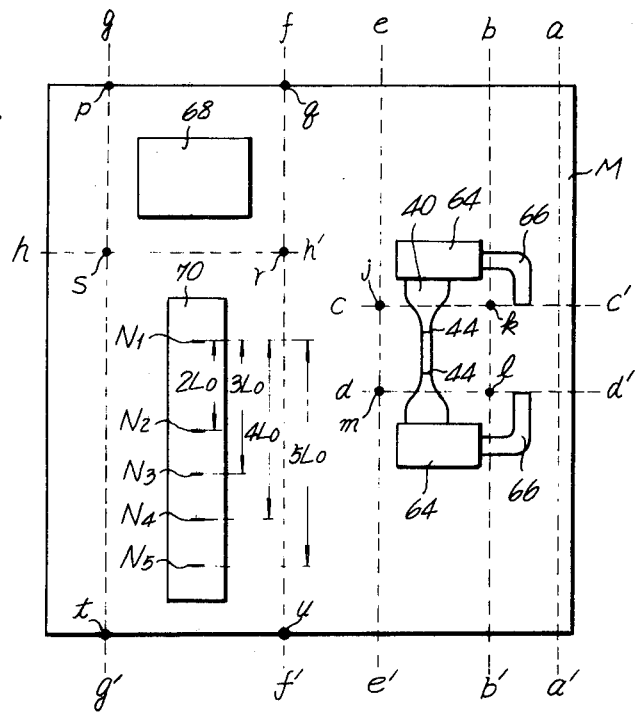
FIG. 4 is a schematic representation of an example of scene to be picked up and translated into an electrical signal in the case where an "area scanner" is employed as the scanning device in the tensile testing system of our invention.

FIG. 4 is a schematic illustration of an example of scene to be picked up and translated into an electrical signal by a television camera or like "area scanner" when same is employed as the scanning device 46 in accordance with our invention. It is of course desirable that within the scene M, only the marking or markings 44 or 44' on the specimen 40 or 40' be of higher lightness than the other surfaces or the background. In practice, however, the scene may include the pair of specimen gripping means 64 and other lusterous metal-made parts that are substantially as light as the marking or markings on the specimen. Although the use of dark covers may be contemplated for hiding such undesired light surfaces, this measure is not desirable since it would make cumbersome the mounting and demounting of specimens on and from the testing machine. The better alternative is to derive from the output signal of the scanning device only its portions representing the region bounded by the dashed lines $j-k-l-m$.

In order to attain the above objective, there may be used the compound "boundary" gate signal which is the logical product of first gate pulses ("longitudinal boundary" pulses) lasting from line $c-c'$ to line $d-d'$ and second gate pulses ("transverse boundary" pulses) lasting from line $e-e'$ to line $b-b'$. Since the transverse boundaries of the region $j-k-l-m$ remain stationary throughout the course of the tensile test, the second gate pulses can be easily produced by utilizing the output from the reference signal generator driving the scanning device.

The durations of the first or longitudinal boundary gate pulses, however, are required to increase with the progress of the test. This requirement can be met by affixing a pair of light-surfaced "longitudinal boundary" members 66 (described later in connection with FIGS. 9 and 11) to the respective specimen gripping means 64 so as to extent transversely therefrom and by forming, with the use of the output from the reference signal generator, auxiliary gate pulses lasting from line $b-b'$ to line $a-a'$. Such auxiliary gate pulses are utilized to extract from the output signal of the scanning device its portions representative of the pair of longitudinal boundary members 66. The thus-extracted signal portions can be utilized to provide the desired longitudinal boundary gate pulses. Thus, since the pair of longitudinal boundary members 66 move relatively away from each other in step with the elongation of the specimen, the durations of the longitudinal boundary gate pulses increase correspondingly.

Another problem that requires consideration with the tensile testing system of our invention concerns the use of a television camera or the like as the scanning device 46. The usual automatic gain control (AGC) of the television camera operates at the brightest area or areas of the scene being picked up, so that its output signal amplitude representing the marking or markings 44 or 44' on the specimen 40 or 40' may become less than the predetermined amplitude limit of the waveform converter 50 of FIG. 1.

This problem can be obviated by the provision of a surface face ("comparison" surface) 68 just as light as the marking or markings on the specimen, with the high lightness comparison surface being immovably disposed within a region bounded by the dashed lines $p-q-r-s$ in FIG. 4. Signal portions representing the comparison surface 68 are derived from the output signal of the television camera for utilization as a comparison signal by its AGC, in order that the output amplitude of the camera representing the marking or markings on the specimen may be in excess of the amplitude limit of the waveform converter 50.

For deriving such portions representing the comparison surface 68 from the television camera output signal, a compound gate signal can be used which is the logical product of transverse boundary pulses lasting from line $g-g'$ to line $f-f$ and longitudinal boundary pulses lasting from line $p-q$ where area scanning is initiated to line $h-h'$. Since the comparison surface 68 can be held stationary throughout the course of the test, the gate signal can be easily produced by utilizing the output from the aforesaid reference signal generator 48.

It is further desirable to provide, between the line $e-e'$ and the line $f-f$ in FIG. 4, a surface (not shown) which is only just as light as the surface of the specimen being tested. The pedestal of the television camera output signal portions representing this unshown surface may be clamped to the zero (black) level, with the result that the output amplitude corresponding to the lightness of the marking or markings on the specimen is unfailingly in excess of the prescribed amplitude limit of the waveform converter. The clamping pulses used for the above purpose can be a simple rectangular wave, with each pulse lasting from line $f-f$ to the line $e-e'$, and can therefore be easily produced from the output from the reference signal generator 48.

Seen at 70 in FIG. 4 is a dark-surfaced "reference length" plate which is intended to prevent the possible decrease in accuracy with which the test region 42 or 42' of the specimen is measured, due for example to the deflection distortion of the television camera or the like or to the change in the frame size with the lapse of time. The reference length plate 70 bears on its dark surface a plurality of reference length marks N1 through N5, spaced apart from each other in the longitudinal direction of the specimen, of the same lightness as the markings 44 or 44' on the specimen.

The reference length marks N2, N3, N4 and N5 are spaced 2Lo, 3Lo, 4Lo and 5Lo, respectively, from the mark N1, where Lo is the initial length of the test region 42 or 42' of the specimen. For deriving from the scanning device output signal those portions which represent the reference length marks N1 through N5, a compound gate signal may be used which is the logical product of transverse boundary pulses lasting from the line $g$-$g'$ to the line $f$-$f'$ and longitudinal boundary pulses lasting from line $h$-$h'$ to line $t$-$u$ where area scanning is finished. This compound gate signal can also be easily produced by utilizing the output from the reference signal generator 48.

For the production of the various gate signals set forth in the foregoing from the output signal or signals of the reference signal generator, there may be employed, for example, monostable multivibrators, differentiators, flip-flops, etc., as described later in further detail in connection with FIGS. 24 and 25.

Figure 5:
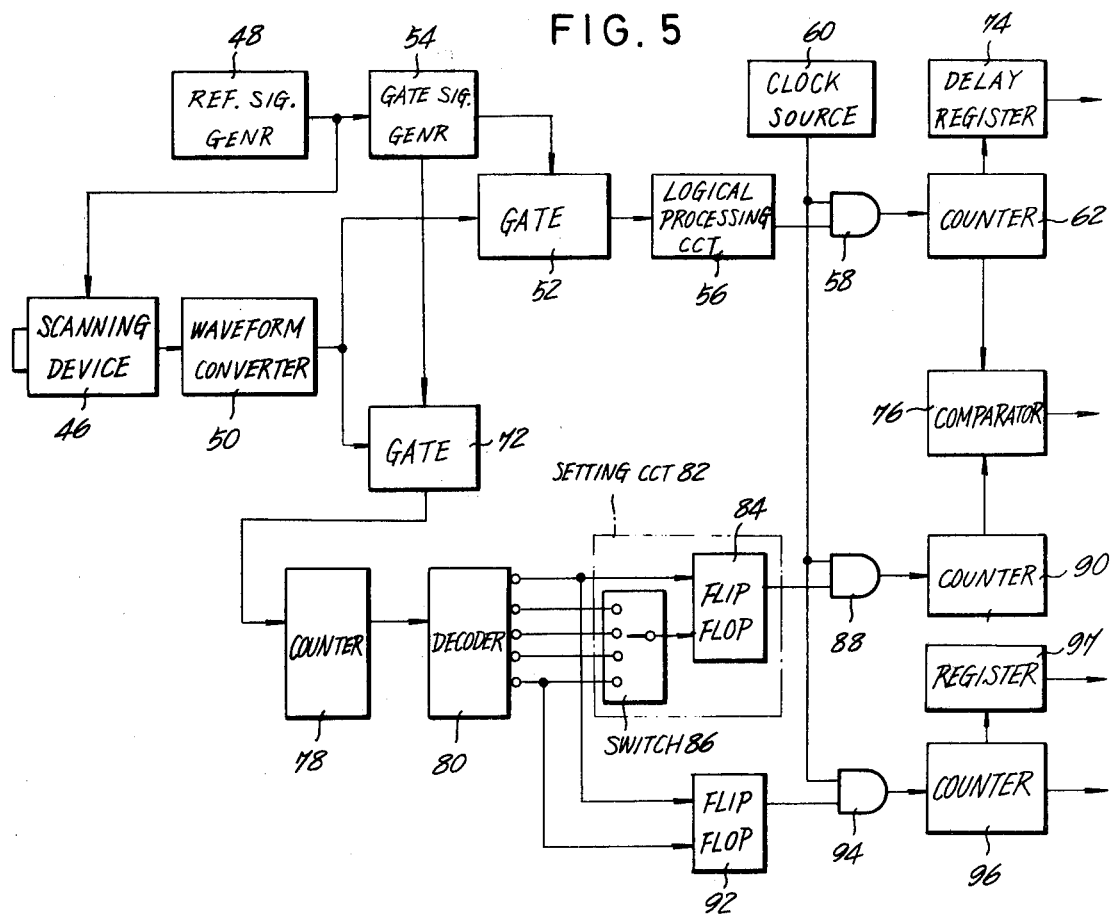
FIG. 5 is a block diagram of another preferred embodiment of our invention.

FIG. 5 illustrates another preferred embodiment of our invention, wherein the scanning device 46 in use can be any such "area scanner" as a television camera, a solid-state "area" image sensor, or a combination of desired "line scanner" and oscillatory or rotary mirror system. The scene to be picked up and translated into an electrical signal by any such scanning device should include at least the specimen 40, for example, and the reference length plate 70 as shown in FIG. 4. It is understood that the scanning device is adapted to scan the scene along lines extending transversely of the specimen 40.

Driven by the output from the reference signal generator 48, the scanning device 46 delivers its electrical output signal to the waveform converter 50 which operates in the manner previously set forth in connection with FIG. 2. The output of this waveform converter is connected to both gate circuits 52 and 72. The gate signal generator 54, also supplied with the output from the reference signal generator 48, produces the aforesaid compound boundary gate signal for deriving from the scanning device output signal only its portions representing the region bounded by the lines $j$-$k$-$l$-$m$ in FIG. 4. This boundary signal is delivered to the gate circuit 52. The gate signal generator 54 is further connected to the other gate circuit 72 for delivering thereto the compound gate signal for deriving from the scanning device output signal its portions representing the region bounded by the lines $r$-$s$-$t$-$u$ in FIG. 4 and including the reference length plate 70.

The tensile testing system of FIG. 5 further comprises the logical processing circuit 56, the AND gate 58, the clock 60, and the counter 62, which are all included in the system of FIG. 2 and which operate in the manner described already. It will therefore be apparent that each time the complete scene is scanned, the counter 62 receives the number of clock pulses representing the length L of the test region 42 of the specimen 40. The counter 62 can be of either the binary or the binary coded decimal type. This counter has its outputs connected to a delay register 74 and to a comparator 74 for delivering thereto the output signals representative of its successive counts.

The delay register 74 is intended for use in ascertaining the ultimate elongation of the test region of the specimen, since the register provides the count made by the counter 62 immediately before the specimen ruptures. The data stored in this delay register are constantly renewed after the lapse of a prescribed time until the specimen ruptures. Thus, even though the count of the counter 62 does not exactly correspond to the length L of the test region 42 at the moment of the specimen rupture, there can be obtained the count made immediately before the specimen ruptures and, therefore, the datum corresponding to the length of the test region at that instant. The strain of the specimen can be computed from that datum and the tensile stress that has been exerted on the specimen at the moment of its rupture.

Figure 6:
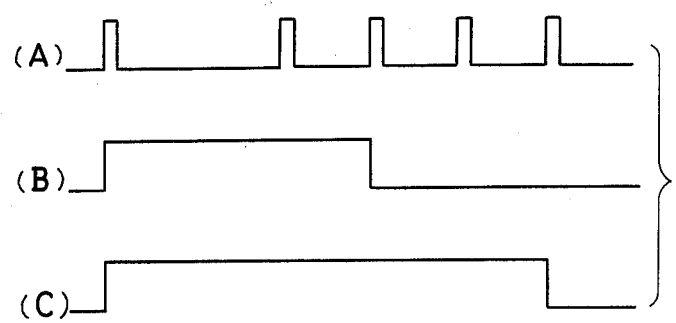
FIG. 6 is a graphic representation of waveforms useful in explaining the operation of the tensile testing system of FIG. 5.

The gate circuit 72 is supplied as aforesaid with the compound gate signal from the gate signal generator 54 for deriving from the scanning device output signal its portions representing the reference length plate 70 as shown in FIG. 4. As graphically represented at A in FIG. 6, the gate circuit 72 produces, each time the complete scene is scanned, an output signal ("reference length mark" signal) including a train of pulses generated at time intervals corresponding to the spacings of the reference length marks N1 through N5 on the reference length plate 70. The time intervals between these reference length mark pulses are subject to change only in the event of improper or irregular scanning of the scene by the scanning device 46.

Further included in the tensile testing system of FIG. 5 is a counter 78 of either the binary or the binary coded decimal type to which is connected the output of the gate circuit 72. This counter counts the reference length mark pulses delivered from the gate circuit 72 and is adapted to be cleared upon each complete scanning of the scene by the scanning device 46.

The output of the counter 78 is connected to a decoder 80 for converting the counts of the counter 78 into those on the decimal basis. The decoder 80 has a plurality of, five in this particular embodiment, output terminals corresponding to the respective reference length marks N1 through N5 on the reference length plate 70. The first or topmost output terminal, as seen in FIG. 5, of the decoder 80 corresponds to the mark N1, the second output terminal to the mark N2, and so forth. High level signals are produced through the respective decoder output terminals when the scanning device 48 scans the corresponding reference length marks, so that during each scanning of the scene, such high level signals are produced sequentially through the decoder output terminals at time intervals corresponding to those between the reference length mark pulses delivered from the gate circuit 72.

The reference numeral 82 in FIG. 5 generally designates a setting circuit for use in ascertaining the tensile moduli of the specimen at various elongations of its test region during the progress of the test. The setting circuit 82 comprises a flip-flop 84 and a multicontact switch 86. The flip-flop 84 has its set input terminal connected to the first or topmost output terminal of the decoder 80 and its reset input terminal to the movable contact of the switch 86. This switch has, in this particular embodiment, four fixed contacts which are connected to the second through fifth output terminals of the decoder 80 respectively.

Thus, if the tensile modulus of the specimen at 200% elongation of its test region is required, for example, the movable contact of the switch 18 may be set to its second fixed contact. The flip-flop 84 will then be set when the first reference length mark N1 on the reference length plate 70 is scanned and will be reset when the third reference length mark N3 is scanned, thereby producing an output signal represented at B in FIG. 6. The duration of the high level portion or pulse of this flip-flop output signal corresponds to the distance between the reference length marks N1 and N3 on the plate 70. The flip-flop 84 is connected to one of the inputs of a two-input AND gate 88 for delivering thereto its output signal as a gate.

Connected to the other input of the AND gate 88 is the clock 60 supplying clock pulses which are to be gated with the output signal of the flip-flop 84. The AND gate 88 has its output connected to a counter 90. It will thus be seen that the number of the clock pulses delivered to the counter 90 during each complete scanning of the scene corresponds to the distance between the reference length marks N1 and N2 when the movable contact of the switch 86 is set to the first fixed contact, to the distance between the marks N1 and N3 when the movable contact is set to the second fixed contact, and so forth.

The counter 90, which can be of identical construction with the counter 62, has its output connected to the comparator 76, to which is also connected the output of the counter 62. Thus, upon agreement of the counts made by the counters 62 and 90, the comparator 76 produces an output signal ("timing" signal) suggestive of the moment for computation of the tensile modulus of the specimen. This timing signal is of course produced when the test region 42 of the specimen 40 is elongated to the percentage to which the setting circuit 82 has been set. Upon production of the timing signal, therefore, the tensile modulus of the specimen may be ascertained by dividing the stress on the specimen by the cross sectional area of the test region.

It may be mentioned that the above timing signal can also be utilized for confirmation of the measuring accuracy of this tensile testing system. To this end a pair of suitable surfaces each bearing a confirmation mark thereon may be held by the respective gripping means of the testing machine. The gripping means may be stopped when the timing signal is produced, and the distance between the pair of confirmation marks may be measured as by means of slide calipers to see if the distance is true to the elongation percentage to which the setting circuit 82 has been set. Preferably, such confirmation should be made for the respective elongation percentages to which the setting circuit can be set. Although the confirmation may be made automatically, manual operation is preferable to omit the necessary electronic circuitry, because it would not often be used. The production of the timing signal may be indicated as by a pilot lamp or buzzer.

The tensile testing system of FIG. 5 further includes a flip-flop 92 having its set input terminal connected to the first output terminal of the decoder 80 and its reset input terminal to the fifth output terminal of the decoder. Each time the scanning device 46 scans the complete scene, therefore, the flip-flop will produce an output signal represented at C in FIG. 6. The duration of the high level portion or pulse of the illustrated flip-flop output signal corresponds to the length of time from the moment the reference length mark N1 is scanned to the moment the mark N5 is scanned. The flip-flop 92 is connected to one of the inputs of a two-input AND gate 94, to the other input of which is connected the clock 60.

Like the above described two AND gates 58 and 88, the AND gate 94 is supplied with the clock pulses from the clock 60, with the result that only those of the clock pulses are permitted to pass through the AND gate which are delivered thereto while the gate signal from the flip-flop 92 is of high level. The AND gate 94 is connected to the input of a counter 96. The number of pulses stored in the register 97 is renewed with each complete scanning of the scene by the scanning device 46.

The value stored in the register 97 is utilized, upon rupture of the specimen 40, to divide the value stored in the register 74, with the quotient being multiplied by a predetermined constant (five in this case) for accurately ascertaining the ultimate elongation of the specimen. While the intervals between the reference length mark pulses change if the scanning raster of the device 46 becomes irregular or if the frame size changes with the lapse of time, the duration of the output pulse of the flip-flop 92 changes correspondingly. Errors in the measurement of the ultimate elongation of the test region for such reasons can be minimized if the total distance of the reference length marks is approximated to the estimated ultimate elongation of the test region, and if the reference length plate is so positioned as to be in side-by-side relationship to the test region of the specimen when same is elongated to the maximum.

Figure 7:
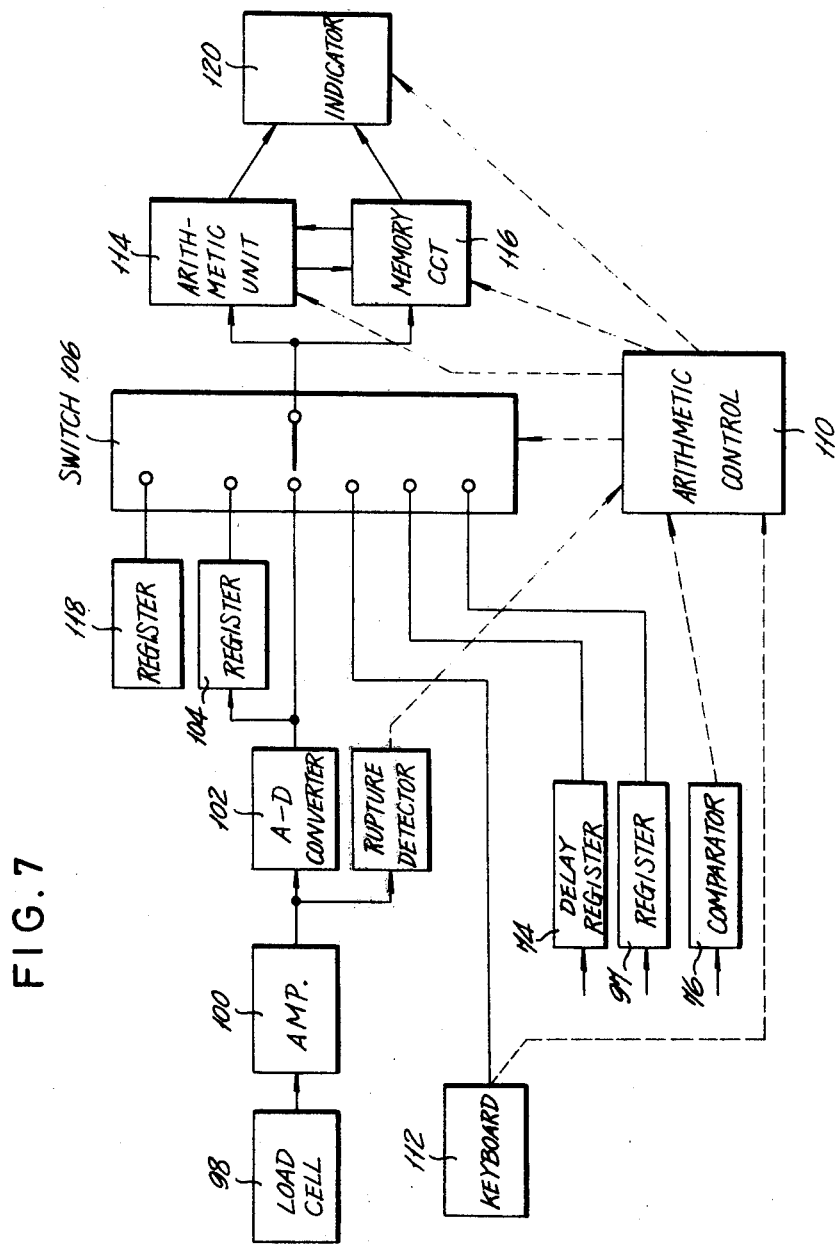
FIG. 7 is a block diagram of a system for automatic processing of signals obtained by the tensile testing system of FIG. 5.

FIG. 7 is a block diagram of an example of system for automatic processing of the data obtained as above through the tensile testing system of FIG. 5. The data processing system includes a load cell 98 for translating the tensile stress on the specimen into an electrical signal. The output of this load cell is connected via an amplifier 100 to an analog-to-digital converter 102, where the amplified load cell output signal is converted into a digital signal representative of the varying stress on the specimen. The output of the converter 102 is connected to a register 104 on the one hand and, on the other hand, to a third fixed contact of a multicontact switch 106.

Like the register 74 of FIG. 5, the register 104 is a delay register for ascertaining the tensile stress on the specimen immediately before its rupture. The data delivered to this delay register are constantly renewed after the lapse of a prescribed time. The output of the delay register 104 is connected to a second fixed contact of the multicontact switch 106.

The output of the amplifier 100 is further connected to a rupture detector 108 for detecting the rupture of the specimen 40. This rupture detector produces an output signal ("rupture" signal) when it detects, through a differentiator or the like, an abrupt change in the output voltage of the amplifier 100 caused by an abrupt decrease in the tensile stress on the specimen as a result of its rupture. The output of the rupture detector 108 is connected to an arithmetic control 110 for delivery of the rupture signal thereto.

Seen at 112 is a keyboard for inputting data such as the cross sectional area of the specimen to an arithmetic unit 114 and memory circuit 116. The output of the keyboard 112 is connected to a fourth fixed contact of the switch 106 on the one hand and, on the other hand, to the arithmetic control 110. This arithmetic control can be operated by actuation of the keyboard.

The multicontact switch 106 operates under the control of the arithmetic control 110, setting its movable contact to any one of the fixed contacts as dictated by the arithmetic control. The switch 106 has its first fixed contact connected to the output of a register 118 adapted to provide a constant required for arithmetic operation. The fifth and sixth fixed contacts of the switch 106 are connected to the registers 74 and 97, respectively, of FIG. 5, and its movable contact is connected to both of the arithmetic unit 114 and the memory circuit 116, so that the length of the test region of the specimen may be computed from the output signals of the registers.

Equipped with a program memory, the arithmetic control 110 is supplied with the output signals of the rupture detector 108, the keyboard 112 and the comparator 76 of FIG. 5, and correspondingly controls the switch 106, the arithmetic unit 114, the memory circuit 116 and an indicator 120 in accordance with a prescribed program.

When the keyboard is operated to input the cross sectional area of the specimen, for example, the arithmetic control 110 responds in the following manner. As the thickness of the specimen is first input through the keyboard, the arithmetic control causes the switch 106 to set its movable contact to the fourth fixed contact and further causes the arithmetic unit 114 and the memory circuit 116 to receive the datum. As the keyboard is subsequently operated to input the width of the specimen, the arithmetic control 110, also instructed from the keyboard that that is the second datum, causes the arithmetic unit 114 and the memory circuit 116 to compute the cross sectional area of the specimen in accordance with the prescribed program and to store the computed value in another location. The arithmetic control 110 further causes the indicator 120 to record and/or indicate the computed cross sectional area of the specimen. If desired, the arithmetic control may cause the indicator to record and/or indicate the thickness, the width, and the cross sectional area of the specimen. The arithmetic control can also be instructed from the keyboard as to a specific percentage or percentages of specimen elongation at which its tensile modulus is to be computed.

The aforesaid rupture signal and timing signal delivered from the rupture detector 108 and comparator 76 to the arithmetic control 110 are therein dealt with as "interruption signals". When supplied with these signals, the arithmetic control 110 causes the switch 106 to supply the data stored in the registers 74, 96 and 104 to the arithmetic unit 114 and memory circuit 116. The arithmetic control further causes the arithmetic unit 114 to compute the tensile modulus and so forth from such data and causes the memory circuit 116 to store the various data. All such data can be recorded and/or indicated by the indicator 120. The arithmetic control 110 gives the above instructions in accordance with the preset program.

Electronic computers of known design can be employed for the arithmetic control 110, the arithmetic unit 114, and the memory circuit 116. It may be mentioned that the rupture of the specimen can be detected not only from an abrupt change in the tensile stress on the specimen but also from the output signal of the scanning device, as by sensing an abrupt change in the duration of the pulse representing the length of the test region of the specimen.

Figure 8:
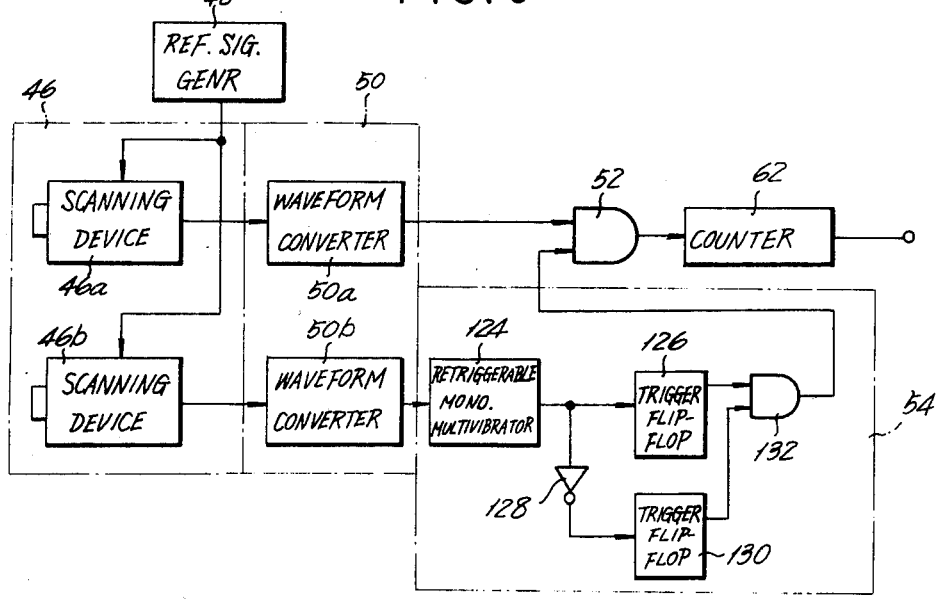
FIG. 8 is a block diagram of a further preferred embodiment of our invention.

In a further preferred embodiment of our invention illustrated in FIG. 8, a pair of solid-state "line" image sensor cameras 46a and 46b are employed as the scanning device 46 for the tensile testing of the specimen 40' shown in FIG. 1A. As seen at A in FIG. 9, this tensile testing system utilizes the aforesaid pair of longitudinal boundary members 66 having surfaces just as light as the marked test region 42' of the specimen. The pair of longitudinal boundary members 66 are affixed to the respective specimen gripping means 64 so as to be situated off the predetermined longitudinal scanning line HS on the specimen 40'. It should also be noted that the opposed ends 122 of the longitudinal boundary members 66 are each situated between one of the gripping means 64 and the test region 42' of the specimen. The distance LL between the opposed ends 122 of the longitudinal boundary members 66 is therefore subject to change in step with the elongation of the test region of the specimen.

The pair of solid-state "line" image sensors 46a and 46b is controlled in synchronism by the output from the reference signal generator 48. The image sensor 46a (hereinafter referred to as the first sensor) is adapted to repeatedly scan the specimen 40' along the line HS extending in its longitudinal direction, whereas the other or second sensor 46b is adapted to repeatedly scan the pair of longitudinal boundary members 66 along the line HSB extending parallel to the scanning line HS.

Figure 9:
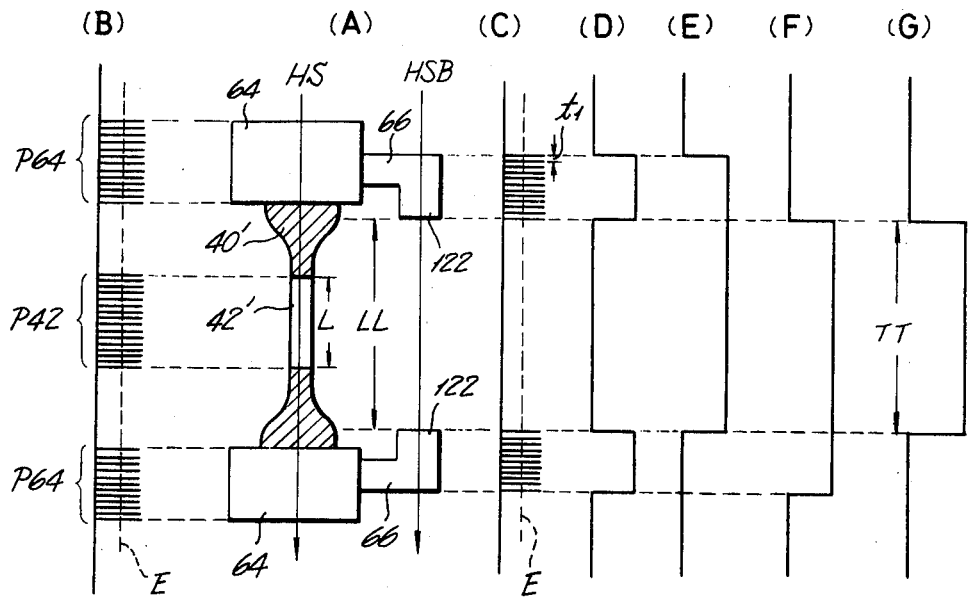
FIG. 9 is a graphic representation of waveforms useful in explaining the operation of the tensile testing system of FIG. 8, with the waveforms being plotted in relation to a specimen being tested and other pertinent means.

If the marked test region 42' of the specimen, the pair of longitudinal boundary members 66 and the pair of specimen gripping means 64 are all light surfaced, and if the unmarked surface portions of the specimen and the background are dark, then the first sensor 46a will produce a signal represented at B in FIG. 9 each time it makes one complete scanning of the specimen along the line HS. This output signal of the first sensor 46a includes a high level portion or pulse train P42 representing the test region 42' of the specimen and two high level portions or pulse trains P64 representing the respective gripping means 64. The second sensor 46b will produce, each time it makes one complete scanning along the line HSB, a signal represented at C in FIG. 9, which includes two high level portions or pulse trains representing the respective longitudinal boundary members 66.

The outputs of the first and the second sensors 46a and 46b are connected to a pair of waveform converters 50a and 50b, respectively, that in combination corresponds to the waveform converter 50 of FIG. 2. The waveform converters 50a and 50b are intended to derive from the respective sensor output signals only their portions above the prescribed level E and to convert them into digital signals. The waveform converter 50a is connected to one of the inputs of the gate circuit 52 which in this particular embodiment takes the form of a two-input AND gate. The other waveform converter 50b is connected to the input of a retriggerable monostable multivibrator 124 which is included in a "longitudinal boundary" gate signal generator circuit corresponding to the gate signal generator 54 of FIG. 2. The time constant of this multivibrator 124 is set slightly longer than the time interval $t1$ of the output pulses of the waveform converter 50b, so that the multivibrator produces a signal represented at D in FIG. 9.

The multivibrator 124 is connected, on the one hand, to the input of a trigger flip-flop 126, by which the multivibrator output signal is converted into the waveform represented at E in FIG. 9. On the other hand, the multivibrator is connected via an inverter 128 to the input of another trigger flip-flop 130, by which the inverted multivibrator output signal is converted into the waveform represented at F in FIG. 9. The flip-flops 126 and 130 are connected to the respective inputs of a two-input AND gate 132 for delivering thereto the signals given at E and F in FIG. 9, with the result that this AND gate produces a signal (longitudinal boundary gate signal) represented at G in FIG. 9. The AND gate 132 is connected to the other input of the AND gate 52, so that this latter AND gate is supplied with both the digital output signal of the waveform converter 50a and the longitudinal boundary gate signal from the AND gate 132. The consequent output pulse of the AND gate 52 are counted by the counter 62.

As will now be apparent, the pulse duration TT of the longitudinal boundary gate signal produced by the AND gate 132 represents the distance LL between the opposed ends 122 of the pair of longitudinal boundary members 66 affixed to the respective specimen gripping means 64 of the testing machine. Furthermore, with the progress of the tensile test, the pulse duration TT increases in step with the elongation of te specimen 40' or of its test region 42', so that only the train of pulses P42 included in the output signal of the first sensor 46a can be delivered to and counted by the counter 62.

Although a pair of image sensor cameras are employed in the system of FIG. 8, there may be used in practice a single optical system behind which two image sensor devices are juxtaposed for scanning along the respective lines HS and HSB under the control of the common output from the reference signal generator. Alternatively, the optical system may be combined with a single image sensor device if means are provided for high speed shifting of the optical system between the two scanning lines.

In cases where "line scanners" other than solid-state "line" image sensors, such as a "line scanning" pickup tube or a combination of a laser scanner and light receptor, are employed as the scanning device 46, the output signals thereof do not take the form of short duration pulse trains, so that the retriggerable monostable multivibrator 124 may be omitted from the longitudinal boundary gate signal generator circuit of FIG. 8. Also, the AND gate 58 and clock 60 of FIG. 2 may be interposed between the AND gate 52 and the counter 62 in the system of FIG. 8, in order that the clock pulses may be gated by the AND gate 58 with the output signal of the AND gate 52, for delivery to the counter 62.

If a television camera or like "area scanner" is employed as the scanning device 46, for scanning the scene shown at A in FIG. 9 along a raster of lines each extending transversely of the specimen 40', then its output signal will be similar to the signals given at B and C in FIG. 9, so that the desired test region signal can be obtained substantially in accordance with the principles of FIG. 8. Since, however, the output signal of the television camera or the like contains both of the portions representing the test region 42' of the specimen and the pair of longitudinal boundary members 66, such signal portions may be separated by utilizing the output from the reference signal generator 48, in accordance with the principles set forth in connection with FIG. 4. The separated signal portions representing the test region of the specimen may be delivered to the AND gate 52 of FIG. 8, and the signal portions representing the longitudinal boundary members 66 may be delivered to the retriggerable monostable multivibrator 124.

Figure 10:
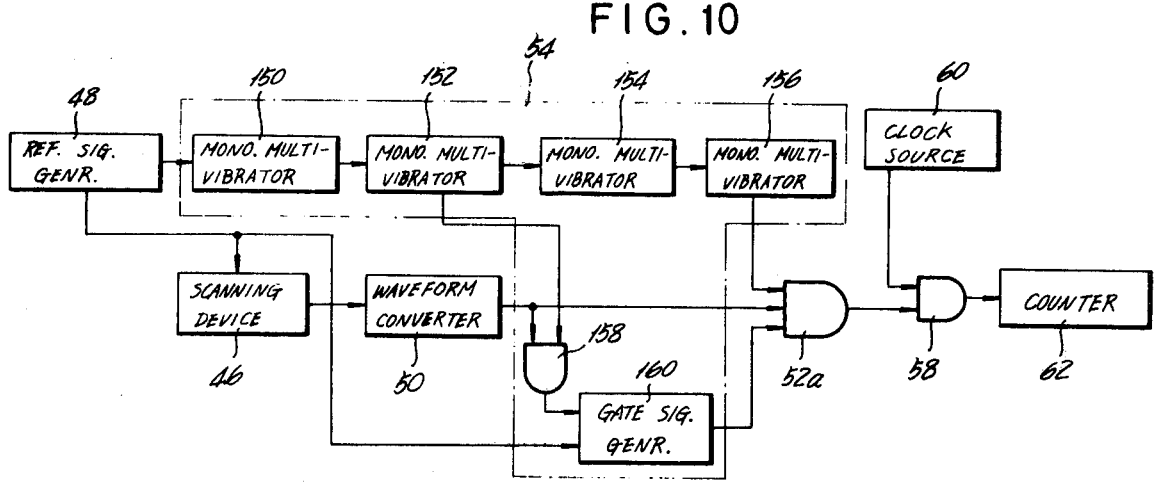
FIG. 10 is a block diagram of a further preferred embodiment of our invention.
Figure 11:
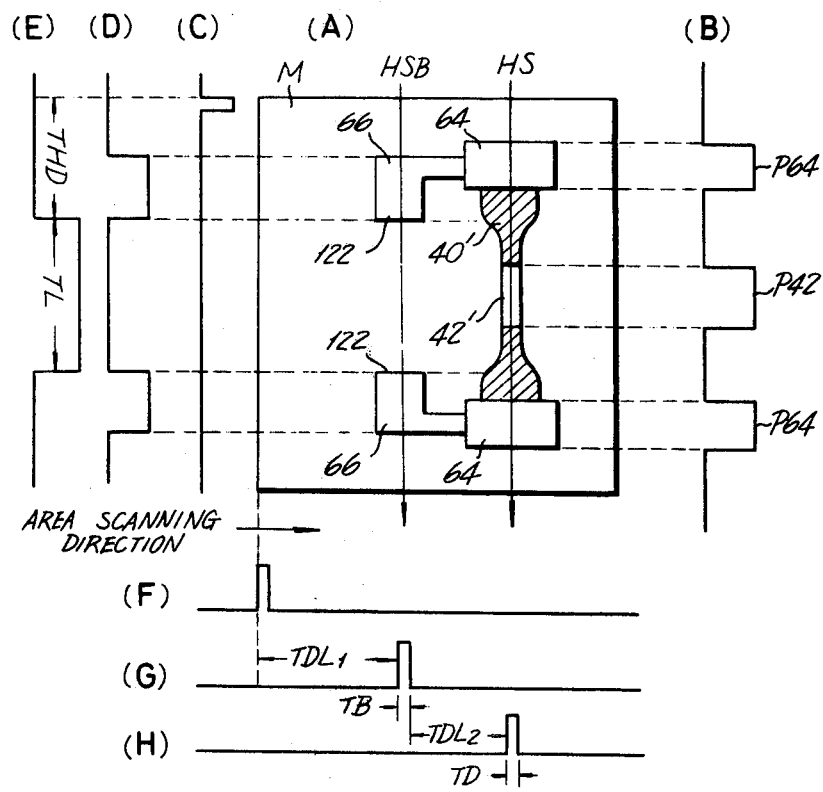
FIG. 11 is a graphic representation of waveforms useful in explaining the operation of the tensile testing system of FIG. 10, with the waveforms being plotted in relation to a specimen being tested and other pertinent means.

FIG. 10 illustrates a further embodiment of our invention, in which a television camera or like "area scanner" is employed for scanning a scene including the specimen 40' of FIG. 1A along a raster of lines each extending in its longitudinal direction, with the lines being scanned sequentially from left to right as viewed in FIG. 11. As shown at A in FIG. 11, the embodiment of FIG. 10 also utilizes the pair of light-surfaced longitudinal boundary members 66 affixed to the respective specimen gripping means 64 of the testing machine.

The scanning device is adapted to scan the specimen 40' along the line HS extending in its longitudinal direction and to scan the pair of longitudinal boundary members 66 along the line HSB. A television camera or the like is of course capable of picking up the several objects within the scene M shown at A in FIG. 11. However, since electrical signal portions representing such objects are not produced simultaneously, but at intervals, the following measure is taken in this embodiment of the invention.

Of all the scanning lines of the television camera or the like on the scene M, those required for the purposes of our invention are only the line HS on the specimen 40' and the line HSB on the pair of longitudinal boundary members 66. The electrical signal portions corresponding to these particular scanning lines must therefore be first taken out of the output from the scanning device. To this end the tensile testing system of FIG. 10 utilizes a "line scanning" reference signal represented at C in FIG. 11 and an "area scanning" reference signal represented at F in FIG. 11, which reference signals are both generated by the reference signal generator 48 driving the scanning device 46.

With reference back to FIG. 10, the scanning device 46 such as a television camera is connected to the waveform converter 50. With each complete scanning of the scene M by the scanning device 46, this waveform converter produces a signal including a portion represented at B in FIG. 11, which corresponds to the scanning line HS, and a portion represented at D in FIG. 11, whih corresponds to the scanning line HSB. Besides being connected to the scanning device 46, the reference signal generator 48 is connected to a serial connection of four monostable multivibrators 150, 152, 154 and 156 included in the gate signal generator circuit 54.

The first monostable multivibrator 150 is triggered by the pulse of the "area scanning" reference signal given at F in FIG. 11 to produce a pulse delayed by a time TDL1. Triggered by this delayed output pulse of the first multivibrator, the second multivibrator 152 produces a pulse of duration TB as represented at G in FIG. 11, thereby causing the third multivibrator 154 to produce a pulse delayed by a time TDL2. Further triggered by this delayed output pulse of the third multivibrator, the fourth multivibrator 156 produces a pulse of duration TD as represented at H in FIG. 11.

It is understood that the delay time TDL1 of the first multivibrator 150 is equal to the length of time from the starting moment of each scanning of the scene M to the moment the line HSB is scanned, so that the output pulse of the second multivibrator 152 is produced just when the line HSB is scanned. This second multivibrator is connected to one of the inputs of a two-input AND gate 158 for delivering thereto the pulse given at G in FIG. 11 as a gate signal. The other input of the AND gate 158 is connected to the waveform converter 50, so that only that portion (given at D in FIG. 11) of the waveform converter output signal is permitted to pass through the AND gate which corresponds to the scanning line HSB.

It is also understood that the delay time TDL2 of the third multivibrator 154 is equal to the length of time from the moment the line HSB is scanned to the moment the line HS is scanned, so that the fourth multivibrator 156 produces its output pulse just when the line HS is scanned. This fourth multivibrator is connected to one of the inputs of a three-input AND gate 52a, which corresponds to the gate circuit 52 of FIG. 2, for delivering thereto the pulse given at H in FIG. 11 as a gate signal. The waveform converter 50 is connected directly to one of the two other inputs of the AND gate 52a. The gate signal from the fourth multivibrator 156 is intended to derive from the waveform converter output signal its portion (given at B in FIG. 11) corresponding to the scanning line HS.

The gate signal generator circuit 54 in the system of FIG. 10 further includes a longitudinal boundary gate signal generator 160 which produces a gate signal for deriving from the waveform converter output signal portion given at B in FIG. 11 the pulse P42 representing the test region 42' of the specimen 40'. For this purpose the gate signal generator 160 utilizes the output signal of the AND gate 158 first to produce a signal represented at E in FIG. 11, and after the time TDL2, to reproduce this signal in synchronism with the scanning of the line HS for delivery to the gate 52a as the longitudinal boundary gate signal.

For producing the signal given at E in FIG. 11 from the output signal of the AND gate 158 given at D in FIG. 11, there can be employed the circuit comprising the trigger flip-flops 126 and 130, the inverter 128, and the AND gate 132 as shown in FIG. 8. For reproducing the FIG. 11E signal after the time TDL2, there may be memorized the times THD and TL from the "line scanning" reference pulse given at C in FIG. 11, so that the signal may be reproduced when the line HS is scanned.

This purpose can be accomplished, for example, by use of four counters. A gate pulse may first be produced whose duration represents the time THD from the leading edge of the "line scanning" reference pulse given at C in FIG. 11 to the leading edge of the pulse given at E in FIG. 11. This gate pulse is utilized for gating clock pulses, and the gated clock pulses are counted by and stored in the first of the four counters. A gate pulse having the duration TL given at E in FIG. 11 is further utilized for gating the same clock pulses, and the gated clock pulses are likewise counted by and stored in the second counter. When the scanning of the line HS is commenced, the same clock pulses may be delivered to the third counter, and the count made thereby may be compared with the count of the first counter. An output produced upon agreement of the counts is utilized to set a flip-flop, and at this moment the same clock pulses are input to the fourth counter. The count made by the latter is compared with the count of the second counter, and an output produced upon agreement of the counts is utilized to reset the mentioned flip-flop. In this manner the signal given at E in FIG. 11 will be reproduced by the flip-flop at the desired time.

It will now be seen that in the tensile testing system of FIG. 10, the three-input AND gate 52a produces the desired test region signal including the pulse P42 seen at B in FIG. 11 each time the scene M is scanned. This test region signal is then delivered to the AND gate 58 for gating the clock pulses supplied by the clock 60, and the output pulses of the AND gate are counted by the counter 62 as in the foregoing embodiments of our invention.

Figure 12:
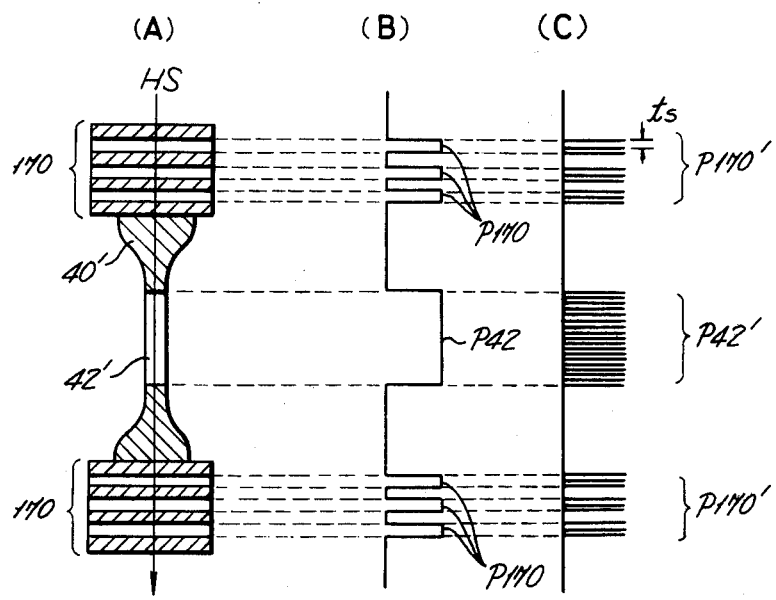
FIG. 12 is a schematic representation of an example of a pair of longitudinal boundary members and a specimen for use with the tensile testing system of our invention, together with a graphic representation of waveforms corresponding thereto.

FIG. 12 is explanatory of another method of extracting the test region signal from the output signal of the scanning device or of the waveform converter. As shown at A in FIG. 12, the specimen gripping means of the testing machine are completely covered by a pair of longitudinal boundary members 170 the surfaces of which are striped to provide alternating light and dark portions each extending transversely of, for example, the specimen 40' of FIG. 1B. Thus, if the specimen 40' together with the pair of longitudinal boundary members 170 is scanned by, for example, a television camera along the line HS extending longitudinally of the specimen, then the waveform converter connected to the camera will produce a signal represented at B in FIG. 12. If a solid-state "line" image sensor is employed, the waveform converter connected thereto will produce a signal represented at C in FIG. 12.

Since, in either case, the output signal of the waveform converter includes a test region signal portion P42 or P42' which is sandwiched between a pair of longitudinal boundary signal portions P170 or P170' having their own characteristic features, the latter signal portions may be decoded by a decoder in order to provide a desired longitudinal boundary gate signal for deriving the test region portion P42 or P42' from the output signal of the waveform converter.

Figure 13:
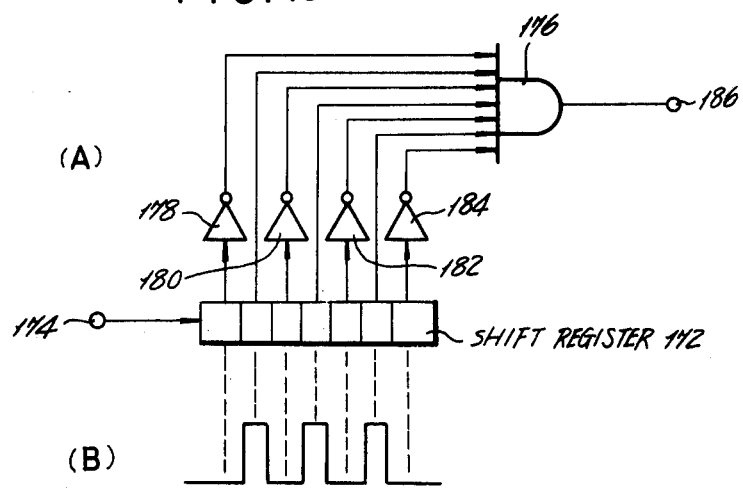
FIG. 13 is a schematic electrical diagram of an example of decoder for use with the longitudinal boundary members of FIG. 12, together with a graphic representation of a waveform corresponding to the longitudinal boundary members.

FIG. 13 illustrates an example of decoder which can be used for the purpose set forth in the preceding paragraph. In the following description of FIG. 13, it is understood that each longitudinal boundary member 170 bears on its surface three light stripes and four dark stripes which alternate as shown at A in FIG. 12, and that a television camera is employed as the scanning device.

The decoder includes a seven-bit, serial-input, parallel-output shift register 172 having an input terminal 174 through which are supplied clock pulses corresponding to the waveform converter output signal given at B in FIG. 12. As will be seen from B in FIG. 13, the recurrence rate of these clock pulses is twice that of the alternating light and dark stripes on the pair of longitudinal boundary members 170. The output terminals of the first, third, fifth and seventh bits of this shift register are connected to the corresponding input terminals of a seven-input AND gate 176 via inverters 178, 180, 182 and 184, respectively, whereas the output terminals of the second, fourth and sixth bits of the shift register are connected directly to the corresponding input terminals of the AND gate. Thus, when the shift register 172 detects the waveform converter output signal portions P170 as shown in FIG. 13, the register delivers high level outputs to the AND gate 176 through all of its input terminals, so that the AND gate produces a high level output from its output terminal 186.

The decoder of FIG. 13 finds use when a solid-state "line" image sensor is employed as the scanning device, as well. However, since in this latter case the waveform converter produces a signal in the form of successions of short duration pulses as given at C in FIG. 12, a retriggerable monostable multivibrator may be connected in the preceding stage of the decoder. The multivibrator is required to have a time constant slightly longer than the time intervals ts of the sensor output pulses, for converting the corresponding waveform converter output signal into the waveform given at B in FIG. 12. It should be understood that the principles of FIGS. 12 and 13 are adoptable when scanning devices other than a television camera or a solid-state "line" image sensor are employed.

Figure 14:
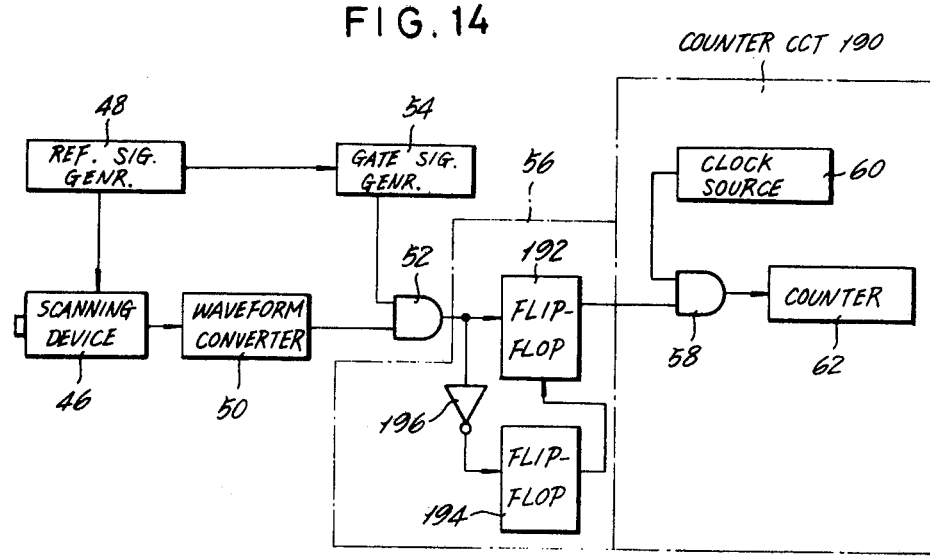
FIG. 14 is a block diagram of a further preferred embodiment of our invention.

FIG. 14 illustrates a further embodiment of our invention, in which a "line scanner" is employed as the scanning device 46, in combination with the specimen 40' of FIG. 1B, and which includes means for deriving the test region portions from the output signal of the waveform converter without use of the longitudinal boundary members.

As in the preceding embodiments of our invention, the embodiment of FIG. 14 includes the scanning device 46 controlled by the reference signal generator 48 for supplying to the waveform converter 50 an electrical signal representing the specimen 40' as well as the pair of specimen gripping means of the testing machine. The output signal of the waveform converter 50 is delivered to the gate circuit or, in this case, a two-input AND gate 52, to which is also delivered the output signal of the gate signal generator 54. The system of FIG. 14 further comprises the logical processing circuit 56 connected to the output of the AND gate 52, and a counter circuit 190 for converting the output signal of the logical processing circuit into data representative of the varying length of the test region of the specimen.

Figure 15:
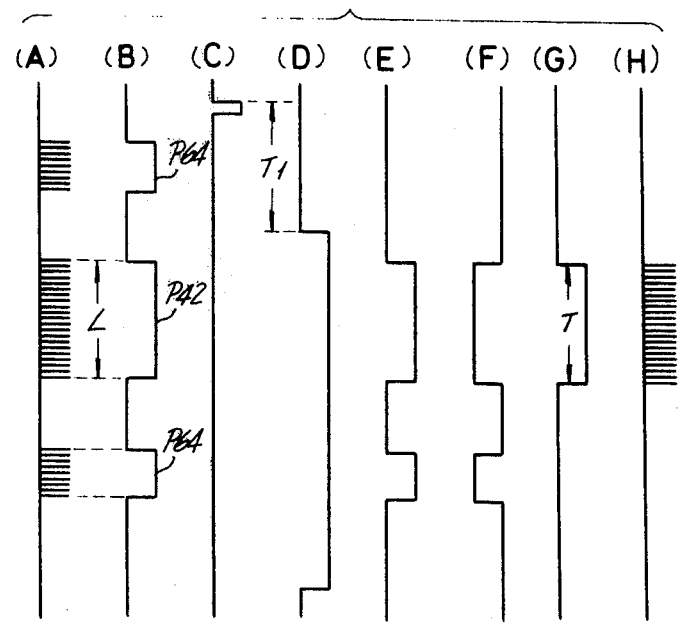
FIG. 15 is a graphic representation of waveforms useful in explaining the operation of the embodiment of FIG. 14.

If the scanning device 46 takes the form of a "line scanning" pickup tube or a combination of a laser scanner and light receptor, the waveform converter 50 will produce a signal represented at B in FIG. 15 each time the specimen 40' is scanned in its longitudinal direction. In the illustrated output waveform of the waveform converter 50, the pulse P42 represents the test region 42' of the specimen, whereas the pulses P64 represent the pair of specimen gripping means 64 (FIGS. 4, 9 and 11) of the testing machine. If a solid-state "line" image sensor is employed as the scanning device 46, its output signal will be as represented at A in FIG. 15, so that in this case, a retriggerable monostable multivibrator may be provided as aforesaid to obtain the signal given at B in FIG. 15.

The gate signal generator 54 of the FIG. 14 embodiment is adapted to produce a gate pulse represented at D in FIG. 15. It will be noted that this gate pulse rises upon lapse of a prescribed time T1 from the rise of the pulse of the "line scanning" reference signal (given at C in FIG. 15) generated by the reference signal generator 48, and decays at the end of each complete scanning of the line extending in the longitudinal direction of the specimen. The time T1 should be so determined that the gate pulse rises just when the specimen portion between its test region 42' and the upper gripping means 64 (as seen in FIG. 11 for example) is being scanned. Thus, delivered to the AND gate 52, the gate pulse of FIG. 15D functions to remove from the waveform converter output signal one of its pulses P64 representing the upper gripping means 64 of the testing machine. The consequent output signal of the gate circuit 52 is represented at E in FIG. 15.

The above AND gate output signal is delivered to the logical processing circuit 56 comprising a first set-reset flip-flop 192 connected directly to the output of the AND gate 52, and another flip-flop 194 connected to the AND gate output via an inverter 196. Delivered to this logical processing circuit, the output signal of the AND gate 52 first sets the flip-flop 192 at each moment the scanning of the specimen test region is initiated. On the other hand the AND gate output signal is inverted by the inverter 196 into the waveform represented at F in FIG. 15. This inverter output signal is delivered to the other flip-flop 194,
setting same by the first rise of its pulses, that is, at the moment the scanning of the specimen test region is completed. The output produced then by the flip-flop 194 is utilized to reset the flip-flop 192, and the subsequent setting of the flip-flop 192 is inhibited.

It is now apparent that the logical processing circuit 56, or its flip-flop 192, produces the desired test region signal represented at G in FIG. 15, with the duration T of its pulse increasing in step with the elongation of the test region 42' of the specimen 40'. The flip-flop 194 is reset upon completion of each scanning of the line. It should be appreciated that the logical processing circuit 56 is well calculated to remove the portion representing the lower specimen gripping means of the testing machine from the output signal of the AND gate 52.

The counter circuit 190 of FIG. 14 embodiment comprises the AND gate 58, the clock 60 and the counter 62 described in connection with FIG. 2. The AND gate 58 gates the output pulses of the clock 60 with the test region signal from the logical processing circuit 56, and the output pulses of this AND gate (given at H in FIG. 15) are counted by the counter 62. There are thus obtained in the counter 62 the desired data, renewed with each complete scanning of the line, that represent the increasing length L of the test region 42' of the specimen 40.

Figure 16:
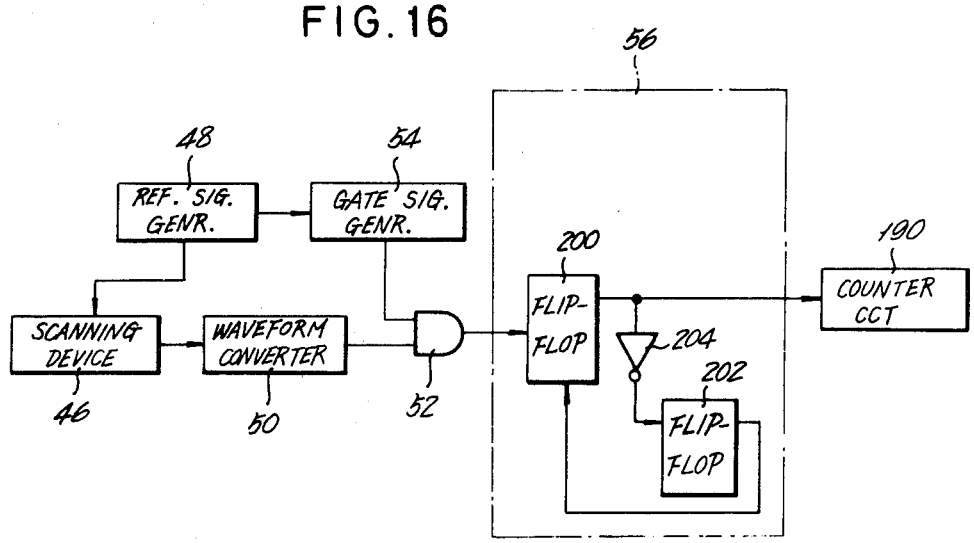
FIG. 16 is a block diagram of a further preferred embodiment of our invention.

FIG. 16 illustrates a slight modification of the preceding embodiment, in which the principles of FIGS. 14 and 15 are applied to the specimen 40 of FIG. 1A. The modification shown in FIG. 16 differs from the FIG. 14 embodiment only in its logical processing circuit 56, which comprises a trigger flip-flop 200 connected to the output of the AND gate 52. The output of the flip-flop 200 is connected to the counter circuit 190 on the one hand and, on the other hand, to the set terminal of another flip-flop 202 via an inverter 204. The output of the flip-flop 202 is connected back to the reset terminal of the flip-flop 200.

Figure 17:
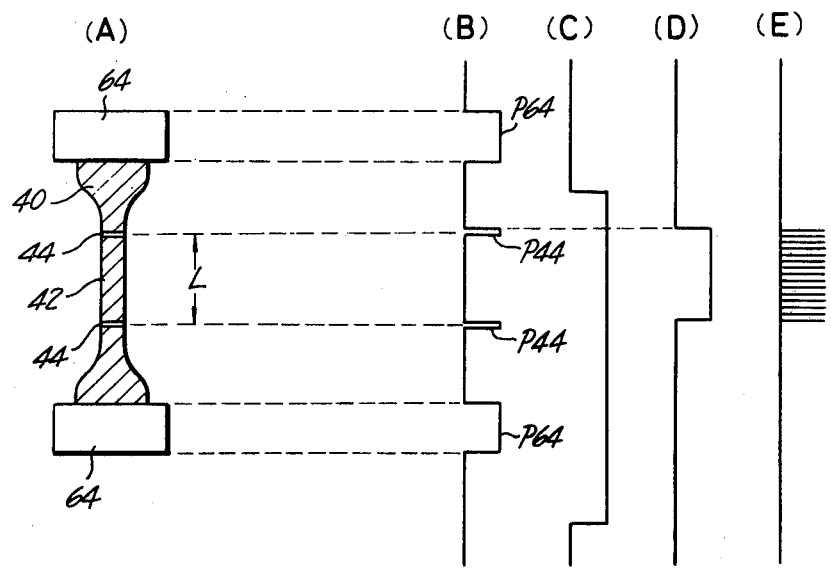
FIG. 17 is a graphic representation of waveforms useful in explaining the operation of the embodiment of FIG. 16, with the waveforms being plotted in relation to a specimen being tested and other pertinent means.

With reference to FIG. 17, since the specimen 40 of FIG. 1A is used in the system of FIG. 16, the output signal of the waveform converter 50 will have the waveform represented at B in FIG. 17, including pulses P64 representing the pair of specimen gripping means 64 of the testing machine and pulses P44 representing the pair of higher lightness markings 44 bounding the test region 42 of the specimen. One of the waveform converter output pulses P64, representing the upper gripping means 64 as seen at A in FIG. 17, is removed by the AND gate 52 with the gate pulse represented at C in FIG. 17, in the manner previously described in connection with FIGS. 14 and 15. This gate pulse is produced in the same way as that given at D in FIG. 15.

As a consequence, the flip-flop 200 of the logical processing circuit 56 produces a pulse which rises when the flip-flop is supplied with the first of the two successive pulses P44 from the AND gate 52 and which decays when the flip-flop is supplied with the next of the pulses P44. The other flip-flop 202 is set upon termination of the output pulse of the flip-flop 200 and resets the latter. The flip-flop 200 thus provides the desired test region signal represented at D in FIG. 17, with the duration of the pulse increasing in step with the elongation of the test region 42 of the specimen 40.

The test region signal produced as above by the logical processing circuit 56 is delivered to the counter circuit 190 the configuration of which can be identical with that shown in FIG. 14. The counter 62 of the counter circuit is thus supplied with the gated clock pulses represented at E in FIG. 17. It will be apparent that the flip-flop 202 is reset upon completion of each scanning operation.

It is to be noted that the boundaries established by the longitudinal boundary signals used in the tensile testing system of our invention should be as close as possible to the elongating test region 42 or 42' of the specimen 40 or 40' throughout the course of the test. According to the various longitudinal boundary signals used in the preceding embodiments of our invention, the longitudinal boundaries established by the signals remain stationary with respect to the specimen gripping means of the testing machine throughout the course of the test. Thus, if the specimen is of rubber or like highly elastic material, "noise" may enter the region bounded by the longitudinal boundary signals with the elongation of the specimen. The "noise" includes, for example, marks (other than those bounding the test region) which have been borne by the specimen, and light which may be reflected by the specimen owing to its flexure if the specimen is gripped irregularly. Such "noise" can seriously interfere with the correct measurement of the test region of the specimen.

Figure 18:
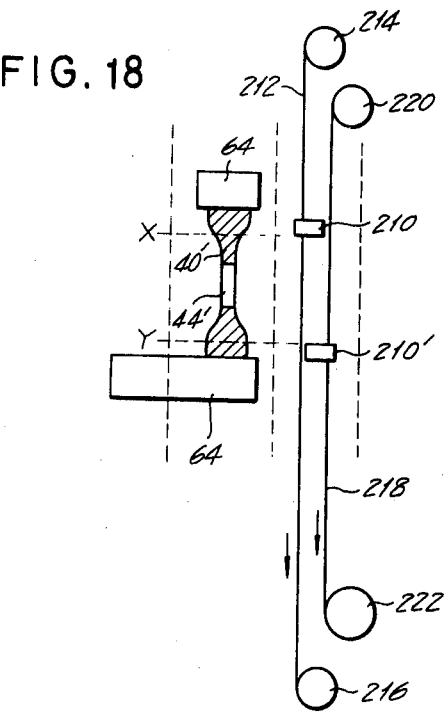
FIG. 18 is a schematic representation of an example of mechanical arrangement for obtaining a longitudinal boundary signal for use in the tensile testing system of our invention.

This problem is thoroughly overcome in a further embodiment of our invention shown in FIG. 18, which includes a pair of light-surfaced longitudinal boundary members 210 and 210' movable in conformity with the elongation of, for example, the specimen 40' of FIG. 1B. The first longitudinal boundary member 210 is affixed to a wire 212 or like flexible, elongate member extending between payoff reel 214 and takeup reel 216 in the longitudinal direction of the specimen, and the second longitudinal boundary member 210' is similarly affixed to a wire 218 or the like extending between payoff reel 220 and takeup reel 222 in the longitudinal direction of the specimen.

As indicated at X in FIG. 18, the first longitudinal boundary member 210 is so mounted on the wire 212 that its bottom edge, as seen in the drawing, is located intermediate between the fixed specimen gripping means 64 and the test region 42' of the specimen 40'. Also, as indicated at Y in FIG. 18, the second longitudinal boundary member 210' is so mounted on the wire 218 that its top edge, as seen in the drawing, is located intermediate between the movable specimen gripping means 64' and the test region of the specimen. The pair of longitudinal boundary members 210 and 210' simultaneously start traveling toward the respective takeup reels 216 and 222 upon commencement of the tensile testing of the specimen 40', but with a difference in speed such that the first longitudinal boundary member 210 travels slower than the second longitudinal boundary member 210'. The traveling speeds of the two members 210 and 210' must be determined in relation to the elongation of the specimen 40', in order that the longitudinal boundaries established by these members may closely follow the elongation of the test region 42' as well as its displacement from the initial position.

The arrangement of FIG. 18 can be adopted in combination with, for example, the tensile testing system of FIG. 8, in which the pair of solid-state "line" image sensors 46a and 46b is employed as the scanning device 46, and in which the longitudinal boundary gate signal is produced by the AND gate 132. If "line scanners" other than the solid-state image sensors are employed as the scanning device 46, the multivibrator 124 may be removed from the system of FIG. 8. In this case, too, the desired longitudinal boundary gate signal is produced by the AND gate 132.

If a television camera or like "area scanner" is employed as the scanning device, the arrangement of FIG. 18 may be used in combination with the system of FIG. 10. It is thus seen that the arrangement of FIG. 18 permits accurate measurement of the test region of the specimen, without being disturbed by the above explained "noise" that might otherwise enter the region bounded by the pair of longitudinal boundary members with the elongation and displacement of the test region.

Figure 19:
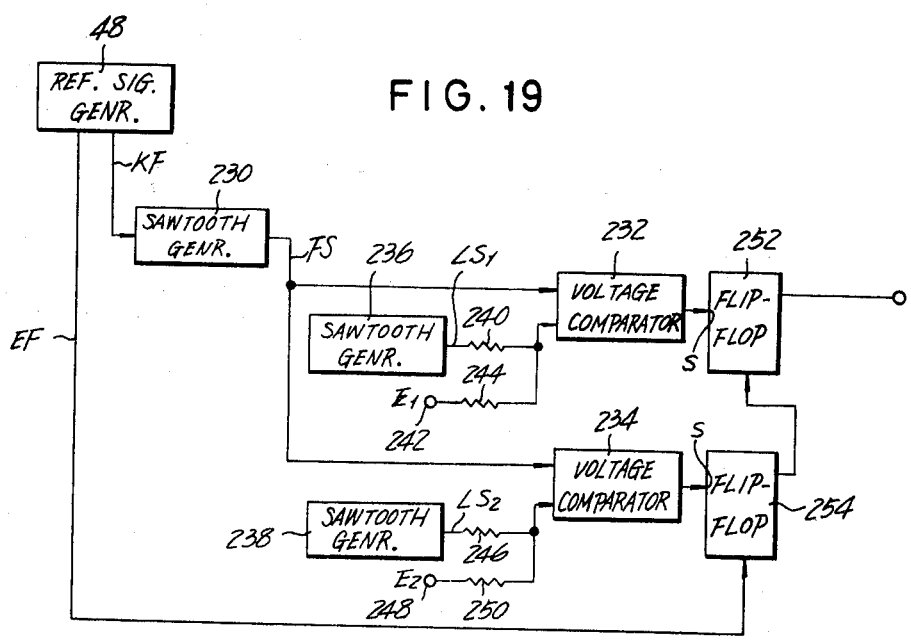
FIG. 19 is a block diagram of an example of means for electrically producing the longitudinal boundary signal.

FIG. 19 illustrates an example of means, for use in the tensile testing system of our invention, for electrically producing a longitudinal boundary gate signal similar to that obtained by use of the arrangement of FIG. 18. The reference numeral 230 in FIG. 19 designates a sawtooth generator which is triggered by the "longitudinal scanning" reference signal KF from the reference signal generator 48 to generate a sawtooth signal FS (FIG. 20) of the same period as each scanning period of the scanning device in the longitudinal direction of the specimen. The output of the sawtooth generator 230 is connected to one of the two inputs of each of a pair of voltage comparators 232 and 234.

A pair of additional sawtooth generators are provided at 236 and 238 for generating sawtooth signals LS1 and LS2, respectively, of the period lasting from the start to the end of the tensile test. The output of the sawtooth generator 236 is connected to the other input of the voltage comparator 232 via resistor 240, to which is also connected a DC supply terminal 242 via resistor 244. The output of the other sawtooth generator 238 is connected to the other input of the voltage comparator 234 via resistor 246, to which is also connected a DC supply terminal 248 via resistor 250. Voltages E1 and E2 are supplied through the respective supply terminals 242 and 248. The outputs of the voltage comparators 232 and 234 are connected to the set terminals of flip-flops 252 and 254 respectively. The flip-flop 252 has its reset terminal connected to the output terminal of the other flip-flop 254, whereas the latter flip-flop has its reset terminal connected to the reference signal generator 48.

Figure 20:
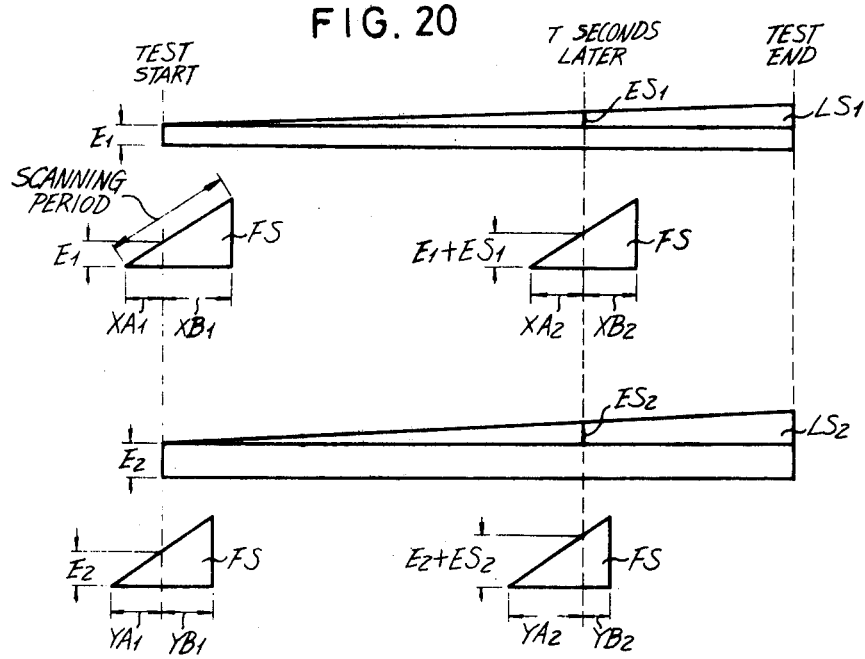
FIG. 20 is a functional waveform diagram explanatory of the operation of the means of FIG. 19.

As will be seen also from FIG. 20, the voltage comparator 232 becomes operative upon agreement of its two input signals to divide the longitudinal scanning period at the ratio of XA1 to XB1. The other voltage comparator 234 becomes operative upon agreement of its two input signals to divide the scanning period at the ratio of YA1 to YB1. The output signals of these voltage comparators 232 and 234 are delivered to the respective flip-flops 252 and 254 through their set terminals. The flip-flop 252 is reset by the output signal of the flip-flop 254, and this flip-flop 254 is reset by a "longitudinal scanning end pulse" EF delivered from the reference signal generator 48.

Figure 21:
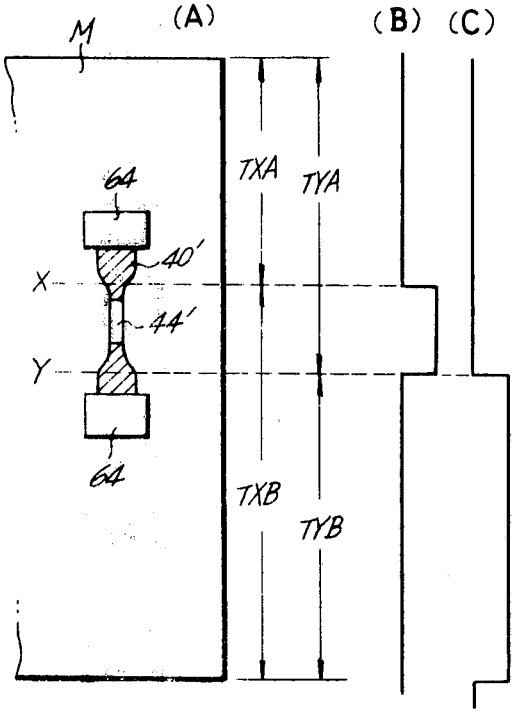
FIG. 21 is a graphic representation of waveforms useful in explaining the operation of the means of FIG. 19, with the waveforms being plotted in relation to a specimen being tested and other pertinent means.

With reference directed also to FIG. 21, the voltage E1 supplied through the supply terminal 242 must be so determined that the upper longitudinal boundary line X, dividing the scene M (seen at A in FIG. 21) into TXA and TXB in accordance with the dividing ratio XA/XB of the longitudinal scanning period, may lie intermediate between the upper specimen gripping means 64 and the test region 42', for example, of the specimen. Similarly, the voltage E2 supplied through the other supply terminal 248 must be so determined that the lower longitudinal boundary line Y, dividing the scene M into TYA and TYB in accordance with the dividing ratio YA/YB, may lie intermediate between the lower specimen gripping means 64 and the test region 42' of the specimen. The supply voltages E1 and E2 thus determine the dividing ratios XA/XB and YA/YB before the start of the test.

During the progress of the test, the voltage comparator 232 becomes operative when the amplitude of the sawtooth signal FS from the sawtooth generator 230 equals the voltage E1+ES1, to set the flip-flop 252. The other voltage comparator 234 becomes operative when the amplitude of the sawtooth signal FS equals the voltage E2+ES2, to set the flip-flop 254. As a consequence, the flip-flops 252 and 254 produce the signals represented at B and C, respectively, in FIG. 21. The leading edge of the output pulse of the flip-flop 252 corresponds to the moment the upper longitudinal boundary line X is scanned, since the voltage comparator 232 becomes operative as above at the moment the longitudinal scanning period is divided into XA2 and XB2 as represented in FIG. 20. The trailing edge of the output pulse of the flip-flop 252 corresponds to the moment the lower longitudinal boundary line Y is scanned, since the voltage comparator 234 becomes operative as above at the moment the longitudinal scanning period is divided into YA2 and YB2, also as represented in FIG. 20.

The amplitudes of the sawtooth signals LS1 and LS2 generated by the pair of sawtooth generators 236 and 238 may be so determined that the boundary lines X and Y may be held at approximately constant spacings from the opposite ends of the test region 42' of the specimen 40' in spite of its gradual elongation and displacement. It will now be apparent that there is produced by the flip-flop 252 the desired longitudinal boundary gate signal similar to that obtained by use of the arrangement of FIG. 18, to make possible the accurate measurement of the test region of the specimen.

In the circuit configuration of FIG. 19, a single sawtooth generator may be employed instead of the pair of generators 236 and 238 if the resistance values of the resistors between the generator and the voltage comparators 232 and 234 are suitably determined. Further, for production of the longitudinal boundary signal before the start of the tensile test, a pair of sawtooth generators 230 may be provided for the respective voltage comparators 232 and 234, instead of utilizing the supply voltages E1 and E2, and these generators may be triggered by respective pulses delayed from the pulse of the longitudinal scanning reference signal KF by the times XA1 and YA1.

Figure 22:
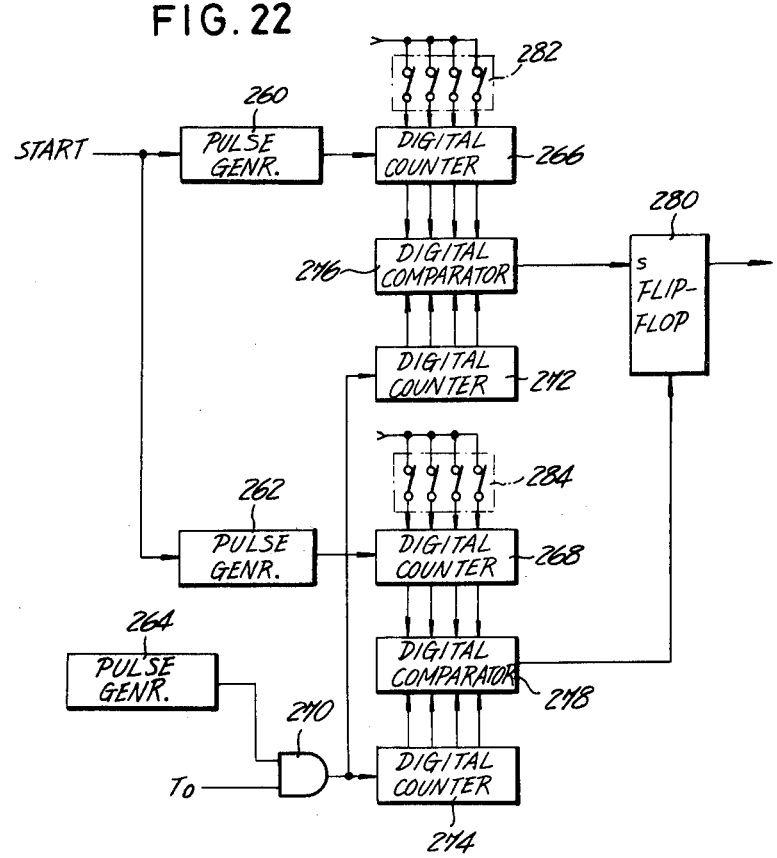
FIG. 22 is a block diagram of another example of means for electrically producing the longitudinal boundary signal.

FIG. 22 illustrates another example of means for electrically (in this case, digitally) producing a longitudinal boundary gate signal similar to that obtained by use of the arrangement of FIG. 18. The circuitry of FIG. 22 includes three pulse generators 260, 262 and 264. The first pulse generator 260 is adapted to generate pulses at an extremely low recurrence rate of, for example, from about a hundred to several hundred pulses throughout the course of the tensile test. The second pulse generator 262 is adapted to generate pulses at a slightly higher recurrence rate. The third pulse generator 264 is adapted to generate pulses at a still higher recurrence rate of, for example, from about a hundred to several hundred pulses during each longitudinal scanning period.

The outputs of the first and the second pulse generators 260 and 262 are connected to the inputs of digital counters 266 and 268, respectively, that are provided with "presetting" input terminals as shown. The third pulse generator 264 is connected to one of the two inputs of an AND gate 270, the output of which is connected to two additional digital counters 272 and 274. The outputs of the digital counters 266 and 272 are both connected to a digital comparator 276, whereas the outputs of the digital counters 268 and 274 are both connected to another digital comparator 278. The output of the digital comparator 276 is connected to the set terminal of a flip-flop 280, and the output of the other digital comparator 278 to the reset terminal of the same flip-flop. The digital counter 266 has a set of switches 282 connected to its presetting terminals respectively, and the digital counter 268 has a similar set of switches 284 connected to its presetting terminals respectively.

Figure 23:
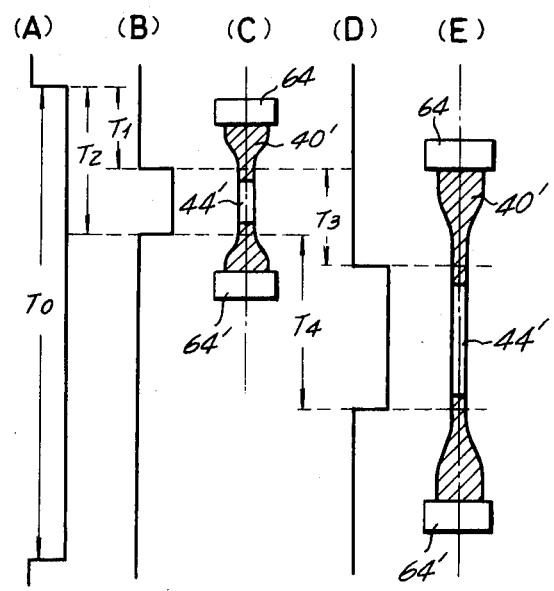
FIG. 23 is a graphic representation of waveforms useful in explaining the operation of the means of FIG. 22, with the waveforms being plotted in relation to a specimen being tested and other pertinent means.

FIG. 23 plots various electrical signals as related in time to the specimen 40', for example, to be tested by the system of our invention including the circuitry of FIG. 22. The signal given at A in FIG. 23 includes a pulse the duration To of which represents one complete longitudinal scanning period of the scanning device in use. This signal is to be supplied to the AND gate 270 through the other of its inputs.

Prior to the tensile testing of the specimen 40', there must be ascertained the number of pulses to be generated by the generator 264 during each scanning period To. On the basis of this pulse number, the numbers of pulses may be computed which correspond respectively to the times T1 and T2 given in FIG. 23. The thus-computed numbers may then be input to the respective counters 266 and 268 by actuating the sets of switches 282 and 284, either manually or through electronic means designed specifically for that purpose, in order that the counters may be preset in conditions as if they had already counted the pulses up to the numbers. (in practice, the signal given at B in FIG. 23 and the output signal of the aforesaid waveform converter may be simultaneously reproduced on an oscilloscope screen, and the numbers to be preset in the counters may be determined so that the pulse of FIG. 23B will completely encompass the test region of the specimen as represented by the waveform converter output signal.)

Upon commencement of the test, the output pulses of the first generator 260 are delivered to the counter 266, and the output pulses of the second generator 262 to the counter 268. The output pulses of the third generator 264 are delivered to the counters 272 and 274 via the AND gate 270 during each scanning period To. The counters 266 and 268 are reset upon completion of the test, whereas the counters 272 and 274 are reset at the end of each scanning period.

The comparators 276 and 278 produce signals when the counts of the counters 272 and 274 agree with the respective preset numbers of the counters 266 and 268 after the start of the test, so that the flip-flop 280 produces the desired longitudinal boundary gate signal given at B in FIG. 23. It will be seen that the pulse of this longitudinal boundary gate signal has its leading edge lying between the upper specimen gripping means 64 of the testing machine and the test region 42' of the specimen 40 and its trailing edge lying between the lower specimen gripping means 64' and the test region 42'.

Moreover, since the counters 266 and 268 are continuously supplied with the output pulses of the generators 260 and 262 throughout the course of the test, the comparators 275 and 278 produce the output signals upon lapse of increasingly longer periods of time from the start of each scanning period To. As a consequence, the moment at which the longitudinal boundary gate pulse is produced changes in accordance with the displacement of the specimen test region 42' away from its starting position. Furthermore, since the recurrence rate of the output pulses of the generator 260 is lower than that of the output pulses of the generator 262, the duration of the longitudinal boundary gate pulse also increases with the progress of the test.

As the test region 42' of the specimen 40' is elongated and displaced from its condition given at C in FIG. 23 to that given at E in FIG. 23, therefore, the leading and the trailing edges of the longitudinal boundary gate pulse are delayed by the times T3 and T4, respectively, from the leading and the trailing edges of the longitudinal boundary gate pulse produced at the start of the test, as will be seen from a comparison of B and D in FIG. 23.

It is now apparent that the longitudinal boundary gate signal similar to that obtained by use of the arrangement of FIG. 18 can also be produced by the digital circuit means of FIG. 22. As may have been noted from a comparison of C and E in FIG. 23, the digital circuit means of FIG. 22 can be employed in conjunction with a testing machine of the type wherein the upper specimen gripping means 64 moves slowly in the same direction as the lower gripping means 64'.

In the circuitry of FIG. 22 the counters 266 and 268 having the presetting terminals can be replaced by usual counters. In this case, however, separate AND gates must be provided for controlling the delivery of the output pulses of the generator 264 to the respective counters 272 and 274, and the gate pulses supplied to these AND gates may be initiated with the delay times of T1 and T2 from the start of the scanning period.

Figure 24:
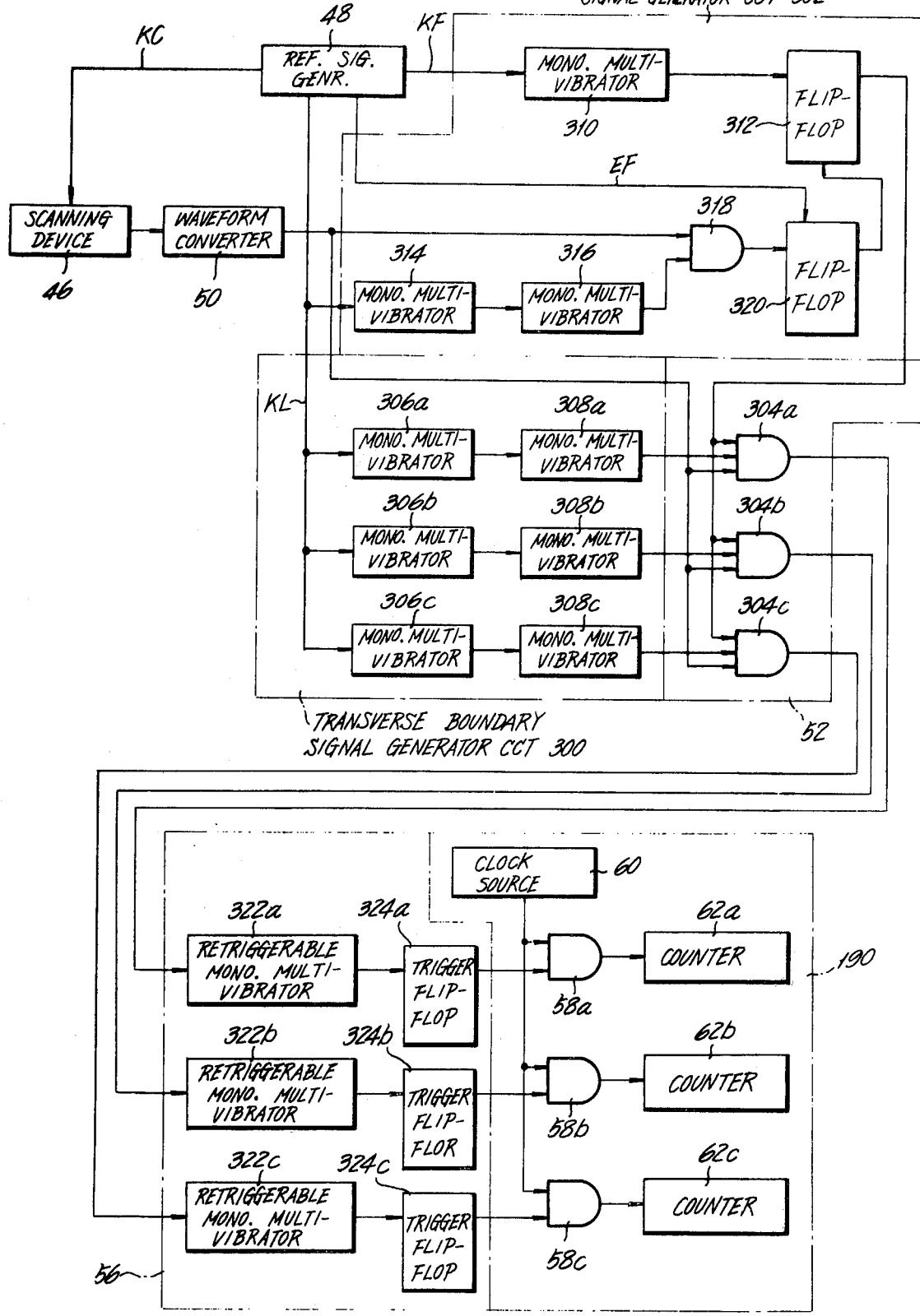
FIG. 24 is a block diagram of a further preferred embodiment of our invention, which is adapted for the simultaneous testing of a plurality of specimens.

A further embodiment of our invention shown in FIG. 24 is adapted for the simultaneous tensile testing of a plurality of, three in this particular embodiment, specimens of the type shown, for example in FIG. 1A.

Broadly, the tensile testing system of FIG. 24 comprises the scanning device 46 in the form of a television camera or like "area scanner", the reference signal generator 48 for driving the scanning device, the waveform converter 50 for converting the output signal of the scanning device into a digital signal, a transverse boundary signal generator circuit 300 for establishing the fixed transverse boundaries for each of the specimens 40, a longitudinal boundary signal generator circuit 302 for establishing the variable longitudinal boundaries common to all the specimens, the gate circuit 52 supplied with the gate signals from the circuits 300 and 302 for deriving from the output signal of the waveform converter its portions corresponding to the test regions 42 of the specimens and their immediate vicinities, the logical processing circuit 56 for converting the output signals of the gate circuit 52 into the test region signals, and the counter circuit 190 of essentially identical configuration with that shown in FIG. 14 and also in FIG. 1.

Figure 25:
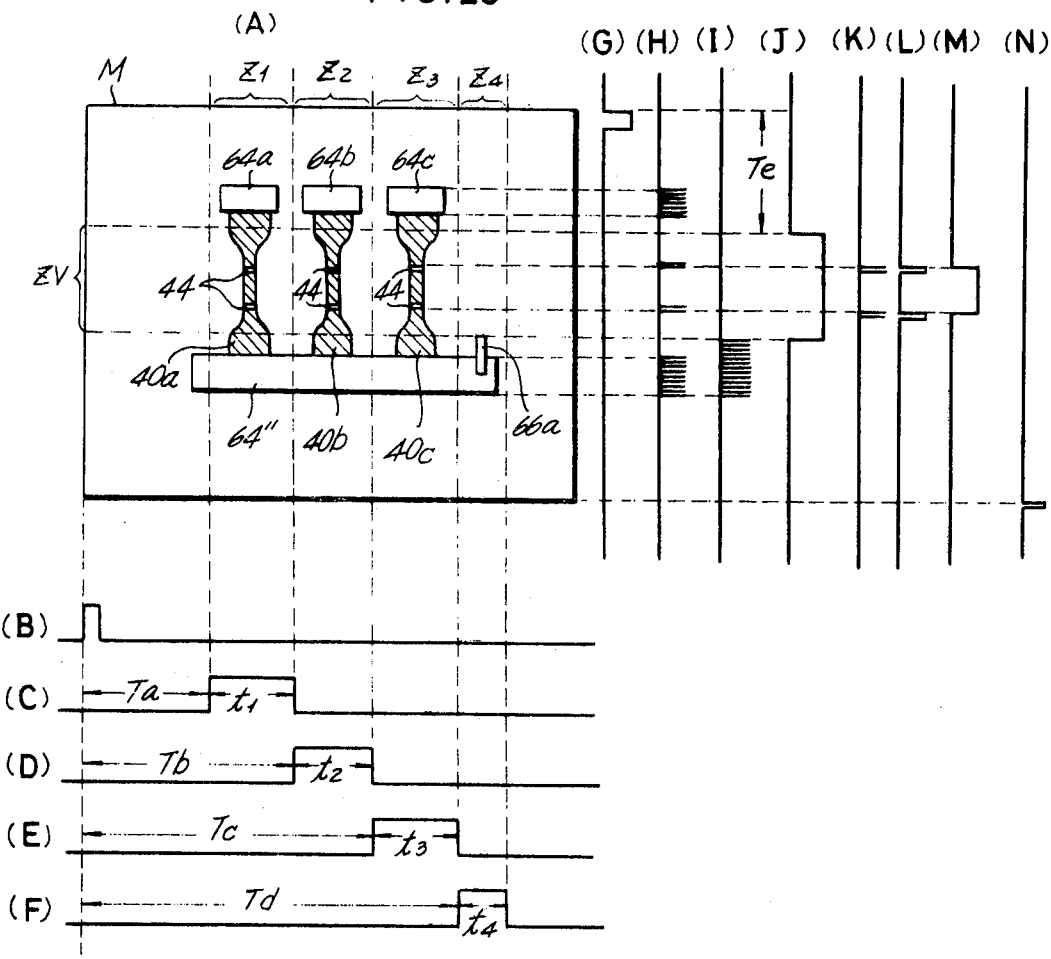
FIG. 25 is a graphic representation of waveforms useful in explaining the operation of the embodiment of FIG. 24, with the waveforms being plotted in relation to the several specimens being tested simultaneously and othe pertinent means.

As shown at A in FIG. 25, the three specimens designated 40a, 40b and 40c are caught at their upper ends by fixed gripping means 64a, 64b and 64c, respectively, and at their lower ends by common movable gripping means 64", of the testing machine so as to be in side-by-side relationship to each other. During the test the movable gripping means 64" is to be moved away from the fixed gripping means 64a, 64b and 64c for simultaneously exerting tensile stresses on the three specimens 40a, 40b and 40c.

A desired "area scanner" employed as the scanning device 46 translates the complete scene M given at A in FIG. 25 by scanning same along a raster of lines extending transversely of the specimens, from left to right of each line and from top to bottom of the successive lines. The reference signal generator 48 is adapted to generate a "line scanning" reference signal (i.e., horizontal synchronizing signal) KL represented at B in FIG. 25 and an "area scanning" reference signal (i.e., vertical synchronizing signal) KF represented at G in FIG. 25 and to deliver to the scanning device 46 a drive signal KC which is compounded of the two reference signals. The reference signal generator 48 is further adapted to generate a reset signal EF, in the form of a pulse of comparatively short duration as represented at N in FIG. 25, at the end of each complete scanning of the frame.

The "area scanner" in use can be either a television camera, a solid-state "area" image sensor, or a combination of laser scanner and light receptor. In either case, as will be apparent from the foregoing explanation, the scanning device 46 will produce a signal represented at H in FIG. 25 each time it scans the complete frame M. The scanning device output signal given at H in FIG. 25, however, includes pulses representing the pair of higher lightness lines or markings 44 bounding the test region of only one of the specimens. During the progress of the test, of course, the scanning device output signal will contain pulses representing the higher lightness lines 44 of all the specimens 40a, 40b and 40c. This scanning device output signal is delivered to the waveform converter 50 and is thereby converted into a digital signal, as in all the preceding embodiments of our invention. The output of this waveform converter is connected, on the one hand, to one of the three inputs of each of three AND gates 304a, 304b and 304c constituting the gate circuit 52.

The transverse boundary signal generator circuit 300 comprises three pairs of monostable multivibrators 306a and 308a, 306b and 308b, and 306c and 308c, with each pair of multivibrators being connected in series with each other. The multivibrators 306a, 306b and 306c have their inputs connected to the reference signal generator 48, and the multivibrators 308a, 308b and 308c have their outputs connected to the AND gates 304a, 304b and 304c, respectively, each through one of the two other inputs of one of the AND gates.

Thus, as the "line scanning" reference signal KL (at B in FIG. 25) is supplied from the reference signal generator 48, the first stage multivibrators 306a, 306b and 306c are simultaneously triggered to introduce delay times Ta, Tb and Tc, respectively, as indicated at C, D and E in FIG. 25. The second stage multivibrators 308a, 308b and 308c are then triggered to produce the desired transverse boundary gate signals having pulses of durations $t1$, $t2$ and $t3$, respectively, also as represented at C, D and E in FIG. 25. As will be apparent from a comparison of A, C, D and E in FIG. 25, the durations of these gate pulses represent the lengths Z1, Z2 and Z3 between the transverse boundaries of the three specimens 40a, 40b and 40c, respectively. The gate pulses are delivered to the respective AND gates 304a, 304b and 304c of the gate circuit 52.

The longitudinal boundary signal generator circuit 302 includes a monostable multivibrator 310 having its input connected to the reference signal generator 48 for receiving therefrom the "area scanning" reference signal KF given at G in FIG. 25. The output of the multivibrator 310 is connected to the set terminal of a flip-flop 312, the output of which is connected to the remaining one input of each of the AND gates 304a, 304b and 304c of the gate circuit 52.

Also included in the longitudinal boundary signal generator circuit 302 are first and second monostable multivibrators 314 and 316 connected in series with each other. The first multivibrator 314 has its input connected to the reference signal generator 48 for receiving therefrom the "line scanning" reference signal KL given at B in FIG. 25. The second multivibrator 316 has its output connected to one of the inputs of a two-input AND gate 318, the other input of which is connected directly to the waveform converter 50. The output of this AND gate is connected to the set terminal of a flip-flop 320, the output of which is connected to the reset terminal of the flip-flop 312. The flip-flop 320 is further connected to the reference signal generator 48 for receiving therefrom the reset signal EF given at N in FIG. 25.

Since the three specimens 40a, 40b and 40c are caught at their upper ends by the fixed gripping means 64a, 64b and 64c, the leading edge of each longitudinal boundary gate pulse (represented at J in FIG. 25) to be produced successively by the circuit 302 can remain static throughout the course of the test. Thus, for determination of the static leading edge of the longitudinal boundary gate pulse, the "area scanning" reference signal is delivered from the generator 48 to the monostable multivibrator 310 for triggering same, with the result that the flip-flop 312 is set after a prescribed time Te (indicated at J in FIG. 25) from the leading edge of the "area scanning" reference pulse. This time Te is of course determined so that the leading edge of the longitudinal boundary gate pulse may represent the upper longitudinal boundary lying between the fixed gripping means 64a, 64b and 64c and the test regions of the specimens 40a, 40b and 40c.

For determination of the variable trailing edges of the successive longitudinal boundary gate pulses, the embodiment of FIGS. 24 and 25 utilizes a light-surfaced longitudinal boundary member 66a, shown at A in FIG. 25, that is affixed to the movable gripping means 64" so as to extend upwardly therefrom and to terminate short of the test regions of the specimens. The first and the second multivibrators 314 and 316 and the AND gate 318 are intended to derive from the waveform converter output signal its portions representing the longitudinal boundary member 66a as well as part of the movable gripping means 64".

The first multivibrator 314 is triggered by the "line scanning" reference signal KL from the generator 48 to introduce a delay time Td, indicated at F in FIG. 25, and the second multivibrator 316 is then triggered to produce a gate pulse of duration t4. The duration t4 of this gate pulse represents the length Z4 between the transverse boundaries of the desired region including the longitudinal boundary member 66a. The gate pulse is delivered to the AND gate 318 for deriving from the waveform converter output signal its portions represented at I in FIG. 25.

The output signal of the AND gate 318 is delivered to the flip-flop 320, with the result that this flip-flop is set at a moment corresponding to the upper end of the longitudinal boundary member 66a. Thus, by resetting the flip-flop 312 with the output signal of the flip-flop 320, the former flip-flop produces the desired longitudinal boundary gate signal which as represented at J in FIG. 25, includes a pulse the duration of which represents the length ZV between the upper and the lower longitudinal boundaries indicated at A in FIG. 25. Since the longitudinal boundary member 66a is carried by the movable gripping means 64", the moment at which the successive longitudinal boundary gate pulses terminates varies in step with the elongation of the specimen. The flip-flop 320 is reset by the signal EF at the end of each complete scanning of the scene M.

The longitudinal boundary gate signal thus produced by the circuit 302 is delivered to the three AND gates 304a, 304b and 304c of the gate circuit 52, to which are also delivered the above explained transverse boundary gate signals from the circuit 300. The pulses of the longitudinal and the transverse boundary gate signals cause each AND gate to produce a signal represented at K in FIG. 25. It will be seen that each AND gate output signal represents the pair of higher lightness lines 44 bounding the test region 42 of the specimens 40a, 40b and 40c.

The logical processing circuit 56 comprises three retriggerable monostable multivibrators 322a, 322b and 322c having their inputs connected to the respective AND gates 304a, 304b and 304c of the gate circuit 52, and three trigger flip-flops 324a, 324b and 324c having their inputs connected to the respective multivibrators 322a, 322b and 322c. Each of the multivibrators 322a, 322b and 322c has a time constant slightly longer than each "line scanning" period of the scanning device 46 in use, so that each multivibrator produces a signal represented at L in FIG. 25. It should be noted that the pair of higher lightness lines 44 on each of the specimens 40a, 40b and 40c are represented by the respective output pulses of the corresponding one of the multivibrators 322a, 322b and 322c.

The output signals of the multivibrators 322a, 322b and 322c are delivered to the respective flip-flops 324a, 324b and 324c and are thereby converted into the aforementioned test region signals represented at M in FIG. 25. The test region signals produced by the flip-flops 324a, 324b and 324c include pulses the durations of which represent the lengths of the test regions of the respective specimens 40a, 40b and 40c.

The counter circuit 190 comprises three AND gates 58a, 58b and 58c each having one of its inputs connected to one of the flip-flops 324a, 324b and 324c of the logical processing circuit 56, the clock 60 connected to the other inputs of the AND gates 58a, 58b and 58c, and three counters 62a, 62b and 62c connected to the outputs of the respective AND gates.

As in the foregoing embodiments, the pulses of the test region signals from the flip-flops 324a, 324b and 324c of the logical processing circuit 56 are utilized as gates for selectively permitting the passage of the clock pulses through the respective AND gates 58a, 58b and 58c. The consequent output pulses of these AND gates are counted by the respective counters 62a, 62b and 62c, so that the counts made by the counters represent the lengths of the test regions of the corresponding specimens 40a, 40b and 40c. It is understood that these counters are reset by the signal EF from the reference signal generator 48 at the end of each complete scanning of the scene M throughout the course of the test.

A plurality of specimens arranged as shown at A in FIG. 25 can also be tested simultaneously by use of a television camera or like "area scanner" adapted to scan the scene along a raster of lines extending in the longitudinal direction of the specimen, with the lines being scanned sequentially from left to right of the scene, as in the embodiment of FIGS. 10 and 11. In this case, as previously explained in connection with FIG. 11, means may be provided for reproducing the longitudinal boundary gate signal each time one of the specimens is scanned and hence for deriving from the waveform converter output signal its portions representing the test region and its immediate vicinity of each specimen.

It is also necessary to provide sets of monostable multivibrators 154 and 156 (FIG. 10) in parallel for the respective specimens in order to produce the gate signals for deriving from the waveform converter output signal its portions corresponding to the scanning lines on the respective specimens. In this case the data representing the lengths of the test regions of the specimens are input sequentially to one and the same counter 62, so that the datum corresponding to the test region of each specimen may be selected by taking advantage of the differences between the times when the specimens are scanned. The counter may be reset each time the datum representing the length of the test region of one of the specimens is read.

When the specimen being tested is of rubber, in particular, the accurate length of its test region must be known at various elongations between 100 and 300%, for example, in order to obtain the tensile moduli of the specimen at such elongations. It is also required to accurately ascertain the length of the test region immediately before the rupture of the specimen, which in the case of rubber, usually occurs at its 400 to even 700% elongation. Solid-state "area" image sensors or "line" image sensors, once properly adjusted, retain their measuring accuracy for extended lengths of time. It is desirable, however, to provide the aforesaid "reference length" plate in the adjacency of the specimen, in view of the possibility that the distance between specimen and scanning device may change for some reason or other during the course of the test.

With the use of a television camera incorporating a pickup tube as the scanning device, measuring errors might be caused by the change in the frame size due to variations in ambient temperature or fluctuations in supply voltage, in addition to the cause set forth in the preceding paragraph. It is therefore desirable to compare the length of the test region of the specimen, as measured through the television camera, with the corresponding reference length as measured through the same camera and hence to see if the test region is being measured correctly. Such comparison is also desirable in cases where a laser scanner is employed as the scanning device, for either the "line" or "area" scanning of the specimen, since measuring errors may occur owing to some irregularity in electrical drive signal or in the mechanical response of the device.

Figure 26:
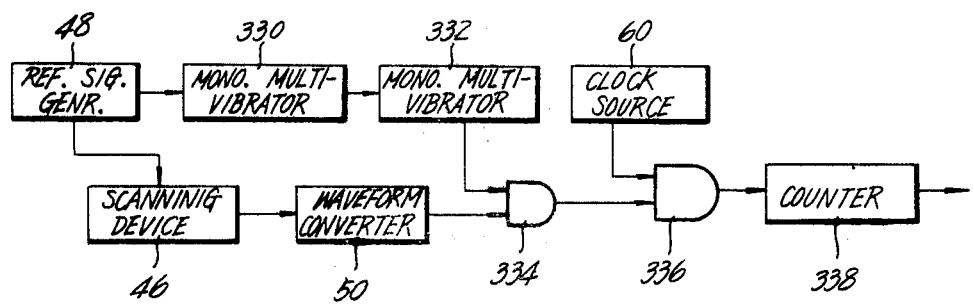
FIG. 26 is a block diagram of an example of means for producing a signal representative of a reference length.

It may be recalled that in the embodiment of FIG. 5, the reference length data for comparison are obtained from the signal representing the marks on the reference length plate 70. FIGS. 26 and 27 illustrate another example of the principles and means for obtaining such reference length data.

According to this additional example, a television camera is employed as the scanning device 46, for scanning the scene M given at A in FIG. 27 along lines extending in the longitudinal direction of the specimen 40' included in the scene, with the lines being scanned sequentially from left to right. Also included in the scene M is a reference length member 70a extending parallel to the specimen 40'. It should be noted that the entire surface of this reference length member is just as light as the test region 42' of the specimen.

The circuitry of FIG. 26 includes the scanning device or television camera 46, the reference signal generator 48, and the waveform converter 50, which are connected as in the preceding embodiments of our invention. The reference signal generator 48 is further connected to the input of a monostable multivibrator 330, which in turn is connected to the input of another monostable multivibrator 332. These multivibrators 330 and 332 correspond to the multivibrators 150 and 152 of FIG. 10. The multivibrator 332 is connected to one of the inputs of a two-input AND gate 334, to the other input of which is connected the waveform converter 50. The AND gate 334 is connected to one of the inputs of another two-input AND gate 336, to the other input of which is connected the clock 60. The output of the AND gate 336 is connected to a counter 338.

It will be seen that the serial connection of multivibrators 330 and 332 is adapted to produce a gate signal represented at C in FIG. 27 by utilizing the "area scanning" reference signal generated by the reference signal generator 48. The pulse of this gate signal corresponds to the scanning line HSK on the reference length member 70a, so that the AND gate 334 operates to derive from the output signal of the waveform converter 50 its portions ("reference length" signal) corresponding to the scanning line HSK. The thus-obtained reference length signal is represented at B in FIG. 27.

The reference length signal is delivered from the AND gate 334 to the other AND gate 336 for gating the output pulses of the clock 60, and the consequent output pulses of the AND gate 336 are delivered to the counter 338. Since the pulse duration TK of the reference length signal given at B in FIG. 27 corresponds to the time during which the reference length member 70a is being scanned in its longitudinal direction, the count made by the counter 338 represents the length L' of the reference length member. This count can therefore be used for comparison with the length L of the test region of the specimen as measured through the same television camera. The counter 338 is understood to be reset upon each complete scanning of the scene M.

The above comparison may be made by means of an electronic computer or a simpler digital comparison circuit or ratio computing circuit. Alternatively, an analog ratio computing circuit may be employed after converting the data into analog signals. While there are no specific limits as to the length of the reference length member 70a, this member may preferably be made longer than the original length of the test region of the specimen, since the corresponding increase in the number of elemental scanning spots corresponding to the member enables more accurate measurement. Also, if the length of the member 70a is made an integral multiple of the original test region length, the comparison will become easier.

The position of the reference length member 70a should be suitably determined in relation to that of the specimen, so as to be substantially in side-by-side relationship thereto. Preferably, since the test region of the specimen gradually shifts from its original position with the elongation of the specimen, the reference length member may be made movable to follow such gradual displacement of the test region.

Alternatively, as depicted in FIG. 28A, a plurality of reference length members 70b may be arranged at longitudinal spacings, or, as depicted in FIG. 28B, a plurality of reference length members 70c may be arranged at longitudinal and transverse spacings in overlapping relationship. In either case the members 70b or 70c may be employed successfully for comparison as the test region undergoes gradual displacement. The illustrated arrangements are particularly effective to overcome the deflection distortion of the scanning device in use.

It is apparent that the test region of the specimen may not be measured correctly if some foreign matter exists in, for example, the region bounded by the lines *j-k-l-m* in FIG. 4. In order to overcome this problem the data obtained during the existence of the foreign matter may be cancelled as being invalid, or means may be provided for discriminating between signal portions representing the test region of the specimen and those representing the foreign matter, as hereinafter described in more detail.

For cancellation of data obtained during the existence of foreign matter in the test region or in the immediate vicinity of, for example, the specimen 40 of FIG. 1A, the number of pulses representing the pair of higher lightness lines or markings 44 bounding the test region (represented at B in FIG. 3) may be counted at the end of each scanning operation to see if the number is equal to the predetermined value. Assuming that the predetermined pulse number is two, only one or no pulse will be produced during each scanning operation if one or both of the higher lightness lines 44 are hidden by some foreign, dark-surfaced object, and three or more pulses will be produced during each scanning operation if some foreign, light-surfaced object or objects exist on or in the adjacency of the test region. Only those data may therefore be considered valid which are obtained when the number of pulses produced during each scanning operation is two.

Figure 29:
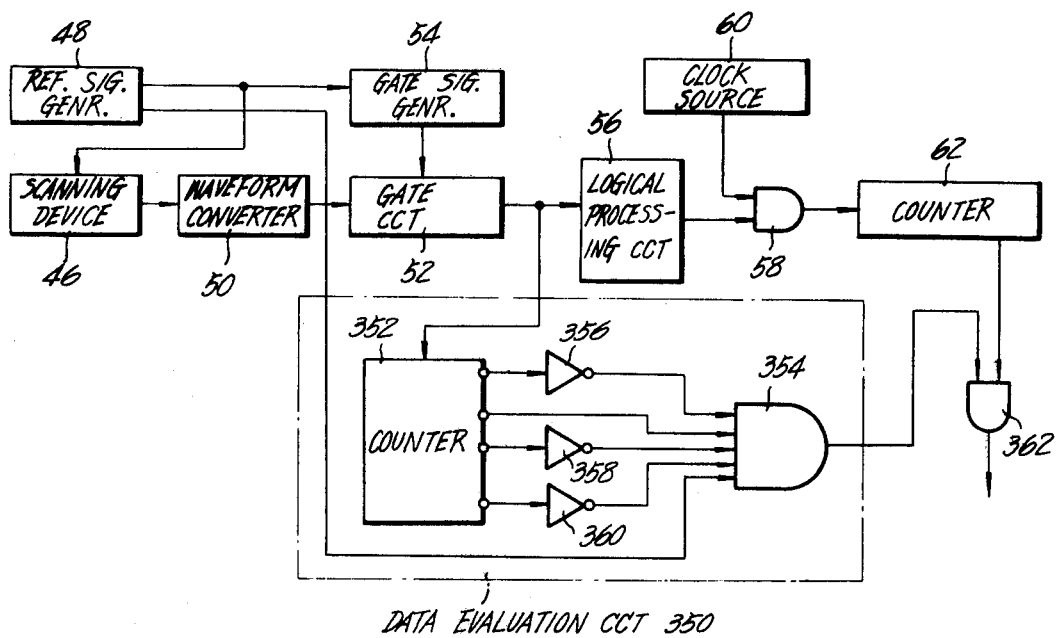
FIG. 29 is a block diagram of a futher preferred embodiment of our invention including a data evaluation circuit.

In a further embodiment of our invention shown in FIG. 29, the tensile testing system of FIG. 2 is equipped with a data evaluation circuit, generally designated 350, for evaluating the validity of the data obtained as to the test region of the specimen. The data evaluation circuit 350 includes a counter 352 of either the binary or the binary coded decimal type having its input connected to the gate circuit 52. The counter 352 has $\frac{1}{2}$, $\frac{1}{8}$ and 1/16 divider stages connected to the separate inputs of a five-input AND gate 354 via inverters 356, 358 and 360, respectively, and a $\frac{1}{4}$ divider stage connected directly to one of the other two inputs of the AND gate. The remaining one input of the AND gate 354 is connected to the reference signal generator 48, and its output is connected to one of the two inputs of another AND gate 362, the other input of which is connected to the counter 62.

The counter 352 counts the number of pulses supplied from the gate circuit 52 during each scanning operation. The reference signal generator 48 delivers to the AND gate 354 a pulse, represented at F in FIG. 30, at the end of each scanning operation. This pulse can be produced from the reference signal, represented at H in FIG. 30, used for the longitudinal scanning of the specimen by the scanning device 46.

Figure 30:
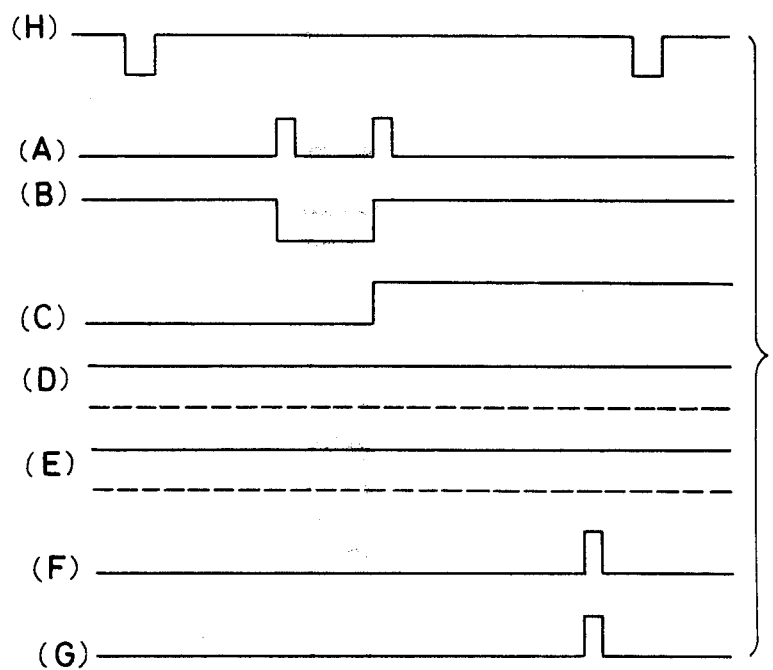
FIG. 30 is a graphic representation of waveforms useful in explaining the operation of the embodiment of FIG. 29.

If the proper number of pulses (two in this case) is produced from the gate circuit 52 during each scanning operation, as represented at A in FIG. 30, then the corresponding outputs from the inverters 356, 358 and 360 will be as represented at B, D and E, respectively, in FIG. 30, and the output from the $\frac{1}{4}$ divider stage of the counter 352 will be as represented at C in FIG. 30. Therefore, the AND gate 354 will produce a pulse represented at G in FIG. 30. This output pulse of the AND gate 354 is of course produced when the gate is supplied with the pulse given at F in FIG. 30 from the gate signal generator 48. It will also be seen that the AND gate 354 produces no pulse in cases where the number of pulses produced from the gate circuit 52 during each scanning operation is other than two.

The output pulse of the AND gate 354 is delivered as a gate to the AND gate 362 for selectively permitting the passage therethrough of the output signal of the counter 62. It is possible in this manner to put out the count of the counter 62 only when the proper number of pulses is produced by the gate circuit 52 during each scanning period.

The data evaluation circuit of the foregoing type, however, may not perform its intended function if, for example, one of the higher lightness lines 44 on the specimen 40 is hidden by some dark-surfaced object and if, at the same time, some light-surfaced or reflective object exists in the adjacency of the test region 42 of the specimen. In such cases the data evaluation circuit 350 of FIG. 29 may be replaced by that of another type wherein each count made by the counter 62 is compared with its preceding count or with the average of its several preceding counts, as described in detail hereinbelow.

During the tensile testing of a specimen of any desired material, the length of its test region increases by small increments with the lapse of time until the specimen finally ruptures, and such incremental change in the length of the test region is of course reflected in data obtained through the system of our invention if no foreign matter exists in the test region or in its neighborhood. If it does, however, the data obtained will exhibit an undue increase or decrease in the length of the test region. Each count made by the counter 62 may therefore be compared with its preceding count or with the average of its several preceding counts. The count may safely be judged to be valid if the difference is within a predefined permissible range, and to be invalid if it is not. In the latter case the final valid count or average of counts may be retained until the counter makes a count whose difference therefrom is within the permissible range.

Figure 31:
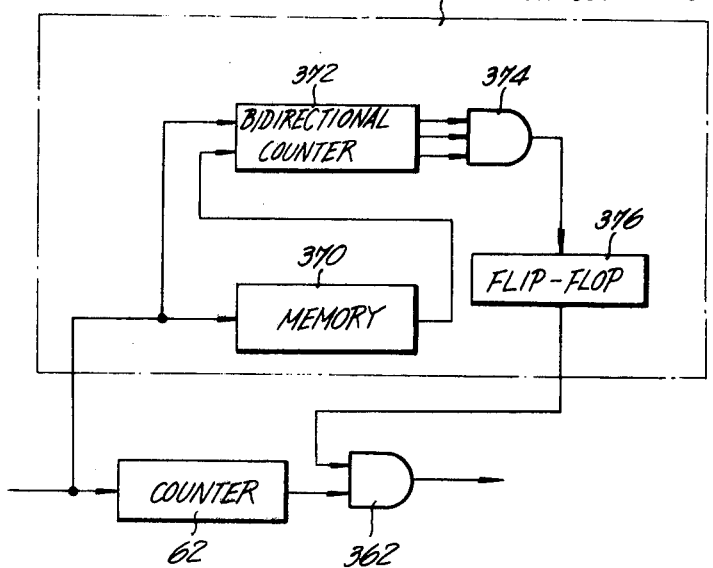
FIG. 31 is a block diagram of another example of data evaluation circuit for use with the tensile testing system of our invention.

FIG. 31 illustrates an example of data evaluation circuit 350a of the above second type, which is shown together with the counter 62 and the AND gate 362 set forth in connection with FIG. 29. The data evaluation circuit 350a includes a memory 370 which in practice can take the form of a shift register or the like and which has its input connected to the AND gate 58 shown, for example, in FIGS. 2 and 29. A bidirectional counter 372 has its add input connected to the AND gate 58 and its subtract input connected to the memory 370. The bidirectional counter 372 is connected to the inputs of an AND gate 374, which in turn is connected to the input of a flip-flop 376. This flip-flop has a negative output which is connected to one of the inputs of the AND gate 362, to the other input of which is connected the counter 62.

Each time the specimen is scanned, the memory 370 receives from the AND gate 58 a train of pulses whose number represents the length of the test region of the specimen, and retains the pulse number until the next scanning operation is completed. During each scanning operation the bidirectional counter 372 also receives the output pulses of the AND gate 58 through its add input and, upon completion of the scanning operation, receives through its subtract input the pulse number of the preceding scanning operation from the memory 370.

The consequent outputs from the bidirectional counter 372 are delivered to the AND gate 374. The bidirectional counter 372 and the AND gate 374 can be so interrelated that the latter may produce an output for setting the flip-flop 376 when the difference between the pulse numbers obtained by two consecutive scanning operations is in excess of the permissible range. Upon setting of the flip-flop 376 the AND gate 362 functions to prevent the passage therethrough of the invalid count made by the counter 62.

There is still another method of evaluating the validity of measurement, by taking advantage of the irregularity that will appear in the output signal of the scanning device 46, or of the gate circuit 52, when some foreign matter exists in the test region of the specimen or in its neighborhood. There may be provided a plurality of memories each having storage locations corresponding to the elementary scanning areas of the scanning device in use. The output signal produced by the scanning device, or by the gate circuit, during each scanning operation may be stored in a different one of the memories, and upon completion of each scanning operation, the signals stored in the memories may be read out simultaneously for delivery to an analog adder. The sum of the signals may then be delivered to an amplitude comparator, which permits the passage therethrough of only those portions of the adder output signal which lie above a prescribed amplitude level. The output from the amplitude comparator can be delivered as a valid signal to the logical processing circuit 56 seen, for example, in FIG. 2.

As the output signals of the several memories are added together by means of the analog adder, those portions of the consequent adder output signal which represent the marking or markings 44 or 44' of the specimen become considerably greater in amplitude than the portions representing foreign matter of transient nature or light reflected the "bleed" or "bloom" of the specimen. Such undesired or invalid signal portions can therefore be removed by suitably setting the amplitude limit of the amplitude comparator connected next to the analog adder. For proper registration of the desired or valid signal portions by the adder in spite of the increasing length of the test region, the scanning period of the scanning device in use may be shortened with respect to the elongation of the test region.

The greater the number of memories in use, the better will be the results obtained. Where a considerably great number of memories are employed, however, delay circuts may be provided to assure proper registration of the valid signal portions in the analog adder. For the most accurate discrimination between valid and invalid signal portions, analog memories such as charge coupled devices may be used for directly storing the analog output signal of the scanning device. For the simplicity of configuration, however, digital memories may be employed for storing the output signal of the gate circuit connected in the succeeding stage of the waveform converter.

Figure 32:
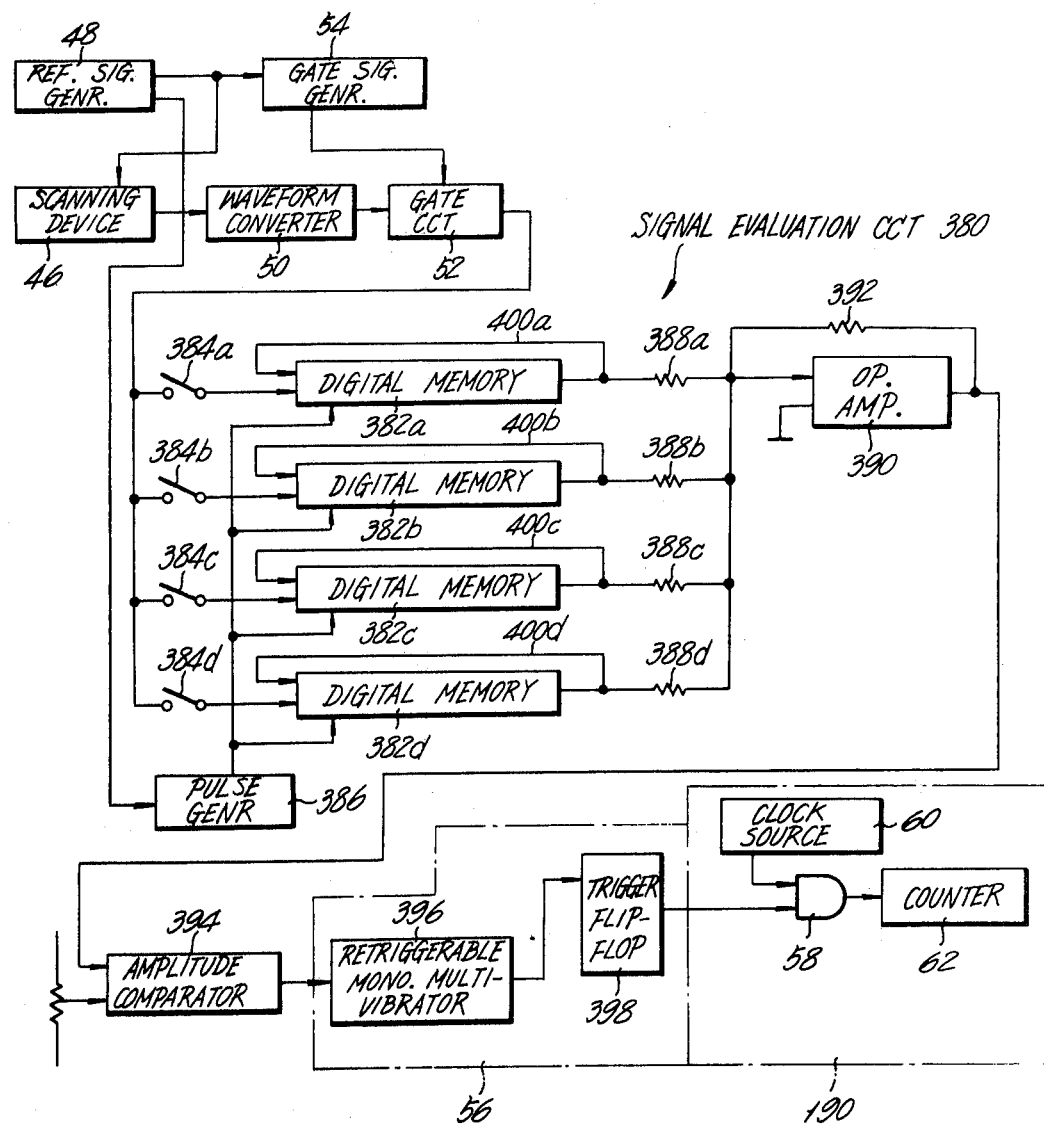
FIG. 32 is a block diagram of a further preferred embodiment of our invention including a signal evaluation circuit.

FIG. 32 illustrates an example of signal evaluation circuit, generally designated 380, for evaluating the validity of the output signal of the gate circuit 52 in accordance with the above described method, with the signal evaluation circuit being shown together with the tensile testing system of our invention. The scanning device 46 of the tensile testing system can be either a television camera adapted to scan the specimen 40 of FIG. 1A along a raster of lines extending in its transverse direction, or a solid-state "line" image sensor.

The signal evaluation circuit 380 comprises a plurality of, four in this embodiment, digital memories 382a, 382b, 382c and 382d connected to the output of the gate circuit 52 via switches 384a, 384b, 384c and 384d respectively. A pulse generator 386 is connected between the reference signal generator 48 and the four memories. The outputs of these memories are connected via respective resistors 388a, 388b, 388c and 388d to one of the inputs of an operational amplifier 390 having a feedback resistor 392 connected between its output and the said one input. The resistors 388a, 388b, 388c, 388d and the operational amplifier 390 constitute in combination an analog adder. The output of the operational amplifier 390 is connected to an analog amplitude comparator 394, the output of which is connected to the logical processing circuit 56 comprising retriggerable monostable multivibrator 396 and trigger flip-flop 398 which are interconnected in series, and thence to the counter circuit 190 comprising AND gate 58, clock 60 and counter 62 which are connected as shown.

As previously set forth in connection with FIG. 2 in particular, the output signal of the scanning device 46 is converted into a digital signal by the waveform converter 50. This digital signal is then gated by the gate circuit 52 to provide a signal representing the test region of the specimen and its immediate vicinity. The output signal of the gate circuit 52 is delivered to the digital memories 382a through 382d via the switches 384a through 384d. Each digital memory can be a shift register with capacity corresponding to all the elemental scanning areas in the test region of the specimen.

During each retrace or flyback time of the scanning device 46, the pulse generator 386 causes the memories 382a through 382d to simultaneously deliver to the analog adder the signal portions that have been stored therein. The data stored in the memories are also fed back to their inputs along feedback lines 400a, 400b, 400c and 400d and are put to repeated use until they are renewed. Since four memories are employed in this embodiment, the data in each memory are renewed each time the complete scene is scanned four consecutive times. The four memories have their data renewed in the order in which the switches 384a through 384d are closed.

Figure 33:
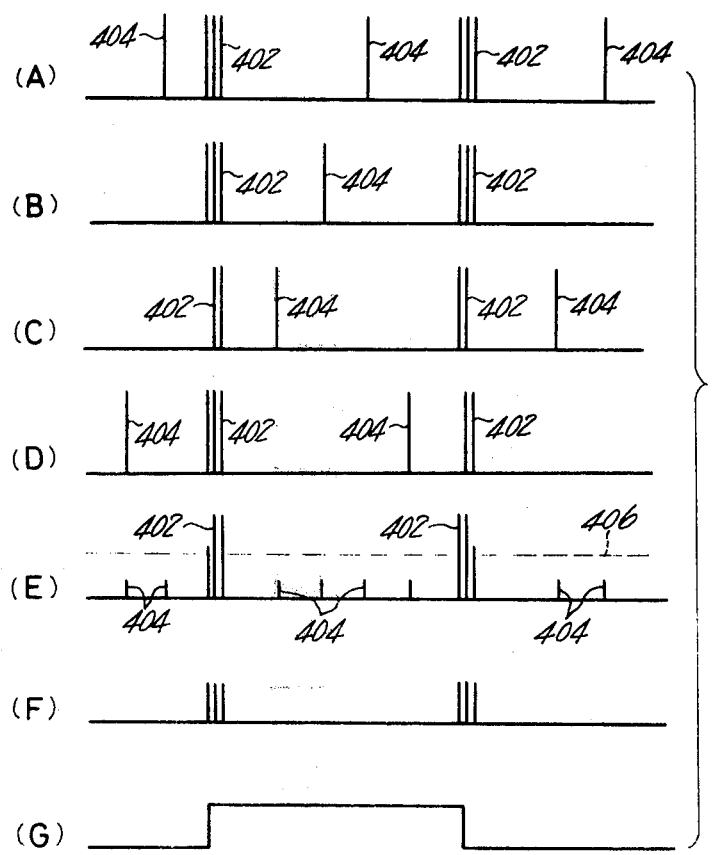
FIG. 33 is a graphic representation of waveforms useful in explaining the operation of the embodiment of FIG. 32.

Graphicaly represented at A, B, C and D in FIG. 33 are examples of the waveforms of the signal portions delivered simultaneously from the memories 382a through 382d to the analog adder including the operational amplifier 390. These waveforms are plotted on the assumption that the output signal of the scanning device 46 has the waveform given at H in FIG. 3. In the waveforms of FIG. 33 pulses 402 represent the pair of higher lightness lines or markings 44 on the specimen 40, and pulses 404 represent some foreign matter.

The output signal of the analog adder is the sum of the signal portions given at A, B, C and D in FIG. 33, so that its waveform will be as represented at E in FIG. 33, in which the amplitude of the signal is shown reduced to facilitate illustration. It should be noted that a significant difference exists between the amplitude of the valid pulses 402 and that of the invalid pulses 404. This is because the valid pulses are invariably produced each time the specimen is scanned, whereas the invalid pulses are produced less often.

In the subsequent analog amplitude comparator 394, only the pulse portions above a predetermined amplitude limit 406 (indicated at E in FIG. 33) are extracted from the output signal of the analog adder, and the extracted signal portions are shaped into the waveform represented at F in FIG. 33. This output signal of the amplitude comparator is delivered to the logical processing circuit 56 and is thereby converted into the test region signal represented at G in FIG. 33, in the manner which is believed clearly apparent from the description of the foregoing embodiments. The test region signal is delivered to the counter circuit 190, in which the counter 62 counts the number of gated clock pulses corresponding to the length of the test region of the specimen.

There can be contemplated additional methods of discriminating between valid and invalid signal portions. According to one such additional method, the recurrence rate or durations of the output pulses of the scanning device can be utilized. If a specimen whose test region has a width of, for example, 5 millimeters is tensioned, the width is reduced only to about 2.5 millimeters or more when the specimen ruptures. Thus, if an "area scanner" is employed for scanning the specimen along lines extending transversely of the specimen, the output signal of the scanning device will include pulses, representing the marking or markings 44 or 44' on the specimen, whose durations are within a certain specifiable range.

These valid pulses may therefore be exaggerated by connecting between scanning device and waveform converter a bandpass filter which permits the passage therethrough of only the fundamental frequency component of the pulsating signal. Alternatively, a pulse duration discriminator circuit may be connected in the succeeding stage of the waveform converter for permittng the passage therethrough of only those pulses whose durations fall within the aforesaid specifiable range.

It will be understood that the above described methods and means for evaluating the validity of measurement are applicable not only to the measurement of the test region of the specimen but to that of reference lengths as well. It may also be mentioned that the accuracy with which the test region of a given specimen is measured can be significantly improved if the scene to be picked up by the scanning device is reduced to an extent just sufficient to cover the test region. With the progress of the test the scanning device may be moved as dictated by the elongation and displacement of the test region.

It is also possible to evaluate the validity of measurement by use of a logical, arithmetic processing circuit which comprises memory means and which operates in accordance with a prescribed program. With the start of the tensile test of a given specimen, the initially obtained value of the length of its test region may be confirmed to be within a predetermined permissible range of variation from the original length of the test region. As the test proceeds, the test region length values obtained by about five to ten consecutive scanning operations may be averaged to determine a permissible range of variation within which the test region length value obtained by the next scanning operation is expected to fall. If the actual value obtained does not fall within this permissible range, the value may be cancelled as being invalid, due for example to the presence of some foreign matter in the test region of the specimen or in its neighborhood.

This method is particularly effective to cancel invalid measurements caused by the presence of foreign matter for an extended length of time. Since the arithmetic processing circuit can be programmed to renew the permissible range of variation within which the test region length value obtained by the next scanning operation is expected to fall, it is possible to accurately determine the valid measurement as such which has been made after the removal or disappearance of the foreign matter. This method is also applicable to the measurement of reference lengths or to other purposes. The manufacture of complex and expensive hardware for the execution of the method can be avoided by use of an available arithmetic processing circuit programmed for the above functions.

Another problem encountered with the tensile testing system of our invention concerns the use of a "line scanner" as the scanning device. The scanning line of the device must be disposed in precise register with the longitudinal median line of the specimen. To this end a pair of suitable marks may be arranged on extensions of the median line with a spacing therebetween and electronic circuit means may be provided to the testing system so that, for example, a pair of pilot lamps corresponding to the marks may be lit up when the "line scanner" is so positioned that its scanning line is in register with the median line, as embodied in the example of FIG. 34 described later.

Alternatively, a sighting telescope may be attached to the "line scanner" in use so that the scanner may be correctly positioned with respect to the specimen as viewed through the telescope. It may also be contemplated to enable the scanner to scan a zone of a certain width extending in the longitudinal direction of the specimen, as by imparting oscillatory motion thereto in the transverse direction of the specimen at a frequency higher than its longitudinal scanning frequency. The same objective may also be attained by use of a semicylindrical lens or of a wide light receptor.

Figure 34:
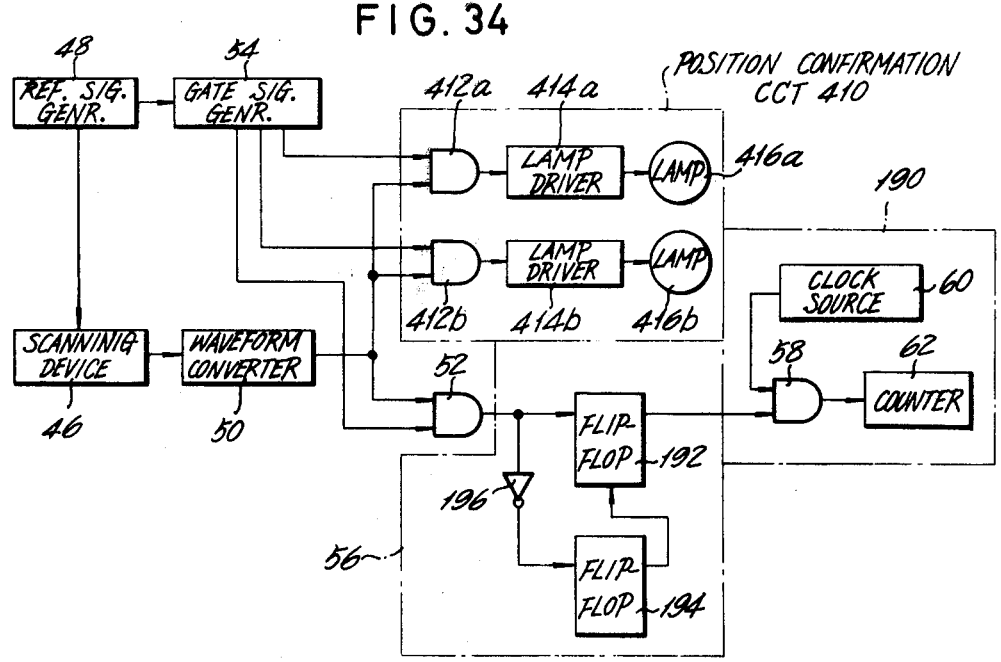
FIG. 34 is a block diagram of a further embodiment of our invention including a position confirmation circuit for permitting accurate positioning of a "line scanner" employed as the scanning device.
Figure 35:
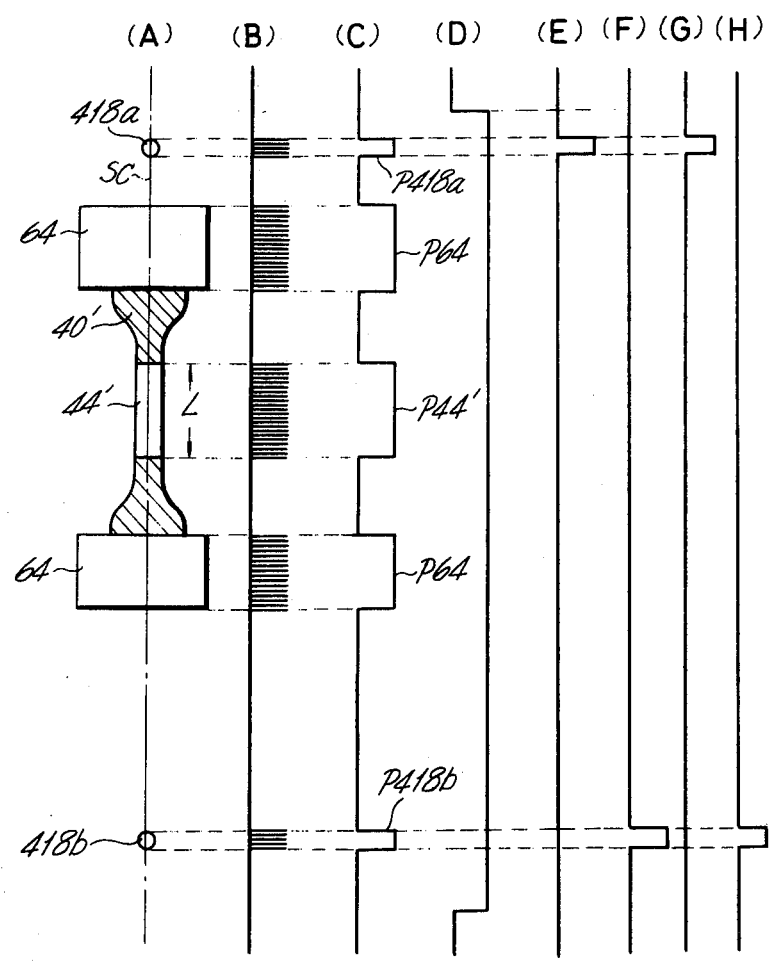
FIG. 35 is a graphic representation of waveforms useful in explaining the operation of the embodiment of FIG. 34, with the waveforms being plotted in relation to a specimen being tested and other pertinent means.

In a further embodiment of our invention shown in FIGS. 34 and 35 the tensile testing system is equipped with the above mentioned electronic circuit means for permitting ready installation in position of a "line scanner" employed as the scanning device. The tensile testing system comprises the scanning device 46, the reference signal generator 48, the waveform converter 50, the gate circuit 52, the gate signal generator 54, the logical processing circuit 56, and the counter circuit 190. The logical processing circuit 56 comprises the flip-flops 192 and 194 and the inverter 196, as in the embodiment of FIG. 14, and the counter circuit 190 comprises the AND gate 58, the clock 60 and the counter 62. The connections of all these circuit components are already described, and their functions are also believed clearly apparent from the foregoing description.

Additionally incorporated in the tensile testing system of the above configuration is a position confirmation circuit 410 for confirmation of the fact that the scanning device 46 is installed in position. The position confirmation circuit 410 includes a pair of two-input AND gates 412a and 412b each having one of its inputs connected to the waveform converter 50. The other inputs of these AND gates are connected to separate outputs of the gate signal generator 54. The position confirmation circuit 410 further comprises a pair of lamp drivers 414a and 414b connected to the outputs of the AND gates 412a and 412b, and a pair of pilot lamps 416a and 416b connected to the outputs of the respective lamp drivers.

The scanning device 46 to be positioned repeatedly scans the specimen 40', for example, in its longitudinal direction under the control of the reference signal generator 48. As depicted at A in FIG. 35, a pair of scanning position marks 418a and 418b of the same lightness as the marked test region 42' of the specimen 40' are disposed on extensions of the median line SC longitudinally dividing the specimen into equal halves.

If the scanning device 46 in use is a combination of a laser scanner and light receptor, its scanning length is determined by the mirror deflecting voltage and by the distance between the scanning device and the specimen. In the case of a solid-state "line" image sensor, the scanning length is determined by the distance between the sensor and the specimen or by the lens system in use. Such factors may therefore be suitably adjusted so that the particular scanning device in use may scan the length covering the pair of scanning position marks 418a and 418b during each scanning period, as will be seen from D in FIG. 35.

Thus, if the scanning device in use is a combination of a laser scanner and light receptor, or a "line scanning" pickup tube, then the signal produced by the waveform converter 50 during each scanning period will be as represented at C in FIG. 35, including pulses P418a and P418b representing the respective scanning position marks 418a and 418b, pulses P64 representing the specimen gripping means 64 of the testing machine, and a pulse P44' representing the higher lightness marking 44' covering the entire test region of the specimen 40'.

If the scanning device in use is a solid-state "line" image sensor, the corresponding output signal of the waveform converter 50 will be as represented at B in FIG. 35. This signal can be converted as aforesaid into the signal given at C in FIG. 35, as by means of a sampling and holding circuit or a retriggerable monostable multivibrator, so that the following description will be made on the assumption that the output waveform of the waveform converter 50 is as represented at C in FIG. 35.

The output signal of the waveform converter 50 is delivered to the pair of AND gates 412a and 412b of the position confirmation circuit 410, each through one of its inputs. The AND gate 412a is further supplied from the gate signal generator 54 a gate signal represented at E in FIG. 35. It will be seen that this gate signal includes a pulse which is delayed by a prescribed time from the start of each scanning period and which corresponds to the moment the scanning position mark 418a is scanned by the scanning device 46. The other AND gate 412b is supplied from the gate signal generator 54 a gate signal represented at F in FIG. 35. This gate signal includes a pulse which is delayed by another prescribed time from the start of each scanning period and which corresponds to the moment the scanning position mark 418b is scanned by the scanning device 46.

If the scanning device 46 is now so positioned as to scan the specimen 40' along its median line SC, the output signal of the waveform converter 50 will include the pulses P418a and P418b representing the pair of scanning position marks 418a and 418b. In that case, therefore, the AND gate 412a will produce a "position confirmation" signal represented at G in FIG. 35, and the other AND gate 412b will similarly produce a position confirmation signal represented at H in FIG. 35. The AND gates 412a and 412b deliver the position confirmation signals to the respective lamp drivers 414a and 414b thereby causing same to light up the respective pilot lamps 416a and 416b. If the scanning device 46 is misplaced, with its scanning line out of register with the median line SC of the specimen 40', then the output signal of the waveform converter 50 will not include the pulses P418a and P418b, so that the pair of pilot lamps 416a and 416b will remain unlit.

It is thus seen that the pair of pilot lamps 416a and 416b, when both lit up, indicate that the scanning line of the device 46 is in exact register with the median line SC. The scanning line is out of register with the median line if either or both of the pilot lamps are unlit. The necessary adjustment of the scanning device position must of course be effected prior to each test, as necessary, so that both pilot lamps may be lit up, and during the test the fact that the scanning device is held properly positioned can also be confirmed from the lamps. The other details of operation of the tensile testing system of FIG. 34 are believed clearly apparent from the description of the preceding embodiments.

The length to be scanned by the scannng device 46 can be considerably reduced if the scanning position marks 418a and 418b are disposed between the pair of specimen gripping means 64, so as to be hidden by the specimen or some other suitable cover during the test. Alternatively, a plate member bearing the scanning position marks thereon may be held by the pair of gripping means 64 so as to extent therebetween instead of the specimen, and the position of the scanning device may be adjusted while tests are not conducted.

The embodiment of FIGS. 34 and 35 is subject to a variety of additional modifications, For example, a single scanning position mark 418a or 418b suffices in cases where the direction in which a specimen is tensioned and the scanning line of the "line scanner" in use are both exactly perpendicular to the plane of the horizon. Further, a pair of scanning position marks similar to the marks 418a and 418b may be disposed on both sides of the median line SC at prescribed distances therefrom. In this case the scanning device is properly positioned if its output signal does not include portions representing the marks. It will also occur to the specialists to utilize the aforesaid position confirmation signals for automatic positioning of the scanning device, as through a servo-mechanism.

Still further, instead of the marks 418a and 418b, lamps may be provided which are each turned on and off at a predetermined rate, and a signal portion repesenting each lamp may be extracted by means of a filter permitting the passage therethrough of a frequency corresponding to the on-off rate of the lamp. In this manner the signal portions representing the lamps can be clearly distinguished from other portions representing some foreign matter that may be located on the median line of the specimen.

The tensile testing system of our invention was put to actual use to determine the tensile strength, ultimate elongation to rupture, and tensile modulus of rubber specimens, and the results were compared with the corresponding measurements made by means of the prior art Schopper tensile tester. The rubber specimens tested were of the following composition:

| Isoprene rubber | 100 | parts |
|---|---|---|
| High abrasion furnace black | 60 | " |
| Zinc oxide | 5 | " |
| Stearic acid | 3 | " |
| Aging resistor | 1 | " |
| Oil | 15 | " |
| Sulfur | 2 | " |
| Accelerator | 1 | " |

In these comparative tests the Schopper tester was also employed in conjunction with the system of our invention, as means for exerting tensile stresses on the specimens, since the machine permits easy mounting of the specimens and, after each test, ready resetting of the movable specimen gripping means or chuck. A load cell was employed instead of a pendulum scale as a load detector. Measurements were all made by skilled personnel. No significant differences were noted between the average values of the various stress-strain properties tested in accordance with our invention and with the prior art. The results of the comparative tests are as tabulated below.

|  | Invention | Prior Art |
|---|---|---|
| Tensile Strength |  |  |
| Number of specimens | 18 | 16 |
| Average, kg/cm$^2$ | 249.0 | 241.0 |
| Standard deviation | 11.0 | 13.0 |
| Significant difference between the averages | None |  |
| Ultimate Elongation |  |  |
| Number of specimens | 18 | 16 |
| Average, % | 574.0 | 562.0 |
| Standard deviation | 21.0 | 24.0 |
| Significant difference between the averages | None |  |
| Tensile Modulus at 300% Elongation |  |  |
| Number of specimens | 16 | 16 |
| Average, kg/cm$^2$ | 108.0 | 108.0 |
| Standard deviation | 3.0 | 3.0 |
| Significant difference between the averages | None |  |

It is noteworthy that the standard deviations of the measurements made as to tensile strength and ultimate elongation in accordance with our invention exhibited a decrease of from about 10 to 15% in comparison with those of the corresponding measurements in accordance with the prior art. Moreover, whereas the measurements made in accordance with the prior art varied appreciably from individual to individual, no such variation was noted in the measurements made in accordance with our invention.

From the foregoing description it will be apparent that there has been provided an improved tensile testing system especially suitable for testing rubber or other relatively elastic material. Although we have shown and described our invention in terms of several specific embodiments thereof, it will be appreciated that variations and modifications therein and in the components thereof will readily occur to those skilled in the art. Accordingly, our invention should be construed broadly and in a manner consistent with the fair meaning or proper scope of the claims appended hereto.

We claim:

1. A tensile testing system for opto-electronically indicating the stress-strain properties of materials under tension comprising, in combination, scanning means for scanning a test specimen made of a material being tensile tested and a test region of the test specimen subjected to elongation by pulling stresses during tensile testing and for detecting and converting to an electrical output signal an optical characteristic of the test region different from other optical characteristics of other surfaces of the test specimen and developing said output signal as elongation of the test region progresses, circuit means receptive of said output signal for deriving therefrom portions thereof representative of the increasing length of the test region during elongation thereof and said scanning means comprising an area scanner developing a two-dimensional scene including the test specimen.

2. A tensile testing system for opto-electronically indicating the stress-strain properties of materials under tension comprising, in combination, scanning means for scanning a test specimen made of a material being tensile tested and a test region of the test specimen subjected to elongation by pulling stresses during tensile testing and for detecting and converting to an electrical output signal an optical characteristic of the test region different from other optical characteristics of other surfaces of the test specimen and developing said output signal as elongation of the test region progresses, circuit means receptive of the output signal including means comprising gate means deriving from said output signal portions of the output signal representative of the increasing length of said test region during elongation thereof, and boundary signal generator means for applying to said gate means a gating signal corresponding to the period when said test region of the specimen is being scanned by said scanning means, whereby said circuit means and gate means thereof derive only said portions of the output signal representative of the increasing length of the test region of said test specimen.

3. A tensile testing system as claimed in claim 2, wherein said circuit means comprises means to produce pulses the durations of which represent the increasing length of the test region of the specimen.

4. A tensile testing system as claimed in claim 2, wherein said circuit means comprises means to produce trains of pulses the numbers of which represent the increasing length of the test region of the specimen.

5. The tensile testing system as claimed in claim 2, wherein said circuit means comprises means for deriving from the output signal of said scanning means pulses the durations of which represent the increasing length of the test region of the specimen, and means for converting said pulses into trains of pulses the numbers of which represent the increasing length of the test region of the specimen.

6. The tensile strength testing system as claimed in claim 2, wherein the system includes reference signal generator means for driving said scanning means and developing a reference signal, and wherein said boundary signal generator means is receptive of said reference signal to produce said gating signal.

7. The tensile strength testing system as claimed in claim 2, wherein said boundary signal generator means comprises means to produce the gating signal on the basis of time elapsed after the start of the tensile testing of the specimen.

8. The tensile strength testing system as claimed in claim 2, wherein the system includes reference signal generator means for driving said scanning means and developing a reference signal, and wherein said boundary signal generator means is receptive of said reference signal to produce said gating and those portions of the output signal of said scanning means which correspond to the test region of the specimen.

9. A tensile testing system for opto-electronically indicating the stress-strain properties of materials under tension comprising, in combination, scanning means for scanning a test specimen made of a material being tensile tested and a test region of the test specimen subjected to elongation by pulling stresses during tensile testing and for detecting and converting to an electrical output signal an optical characteristic of the test region different from other optical characteristics of other surfaces of the test developing said output signal as elongation of the test region progresses, first circuit means receptive of said output signal for deriving portions thereof representative of the increasing length of said test region, second circuit means for evaluating the validity of said portions of said output signal, and said second circuit having means for preventing development of invalid portions of said output signal.

10. A tensile testing system for opto-electronically indicating the stress-strain properties of materials under tension comprising, in combination, scanning means for scanning a test specimen made of a material being tensile tested and a test region of the test specimen subjected to elongation by pulling stresses during tensile testing and for detecting and converting to an electrical output signal an optical characteristic of the test region different from other optical characteristics of other surfaces of the test specimen and developing said output signal as elongation of the test region progresses, first circuit means receptive of said output signal for deriving portions thereof representative of the increasing length of said test region, and second circuit means for eliminating invalid ones of said portions of said output signal.

11. A tensile strength testing system for use with a specimen having a test region defined in its midportion by at least one marking having a different optical characteristic from the other surfaces of the specimen, wherein the specimen is adapted to be gripped at both ends by a pair of specimen gripping means and to be subjected to increasing longitudinal pulling stress as the pair of specimen gripping means move relatively away from each other, said tensile strength testing system comprising, in combination, a pair of boundary members disposed in spaced-apart positions in a longitudinal direction of the specimen and movable relatively away from each other in relation to the movement of said pair of specimen gripping means, scanning means for translating the optical characteristics of at least the specimen and said pair of boundary members into an electrical signal, said scanning means producing the electrical signal repeatedly with the progress of the tensile testing of the specimen, boundary signal generator means for producing a gate signal representing the varying time when at least the test region of the specimen is being scanned by utilizing portions of the output signal of said scanning means which correspond to said pair of boundary members, and gate means supplied with the output signal of said scanning means and with the gate signal produced by said boundary signal generator means, whereby said gate means derives from the output signal of said scanning means its portions representative of the varying length of the test region of the specimen.

12. A tensile strength testing system as claimed in claim 11, wherein said pair of boundary members have the same optical characteristic as the marking on the specimen and are substantially spaced from the specimen in the transverse direction thereof, and wherein said pair of boundary members have opposed ends each located intermediate between the test region of the specimen and one of the specimen gripping means.

13. A tensile strength testing system as claimed in claim 11, wherein each of said boundary members bears alternating first and second stripes each extending in a transverse direction of the specimen, said first stripes having the same optical characteristic as the marking on the specimen and said second stripes having a different optical characteristic from that of the marking on the specimen.

14. A tensile testing system as claimed in claim 13, wherein said pair of boundary members are attached to the respective specimen gripping means so as to conceal same.

15. A tensile testing system capable of simultaneously testing a plurality of specimens each having a test region defined thereon by at least one marking having a different optical characteristic from other surfaces thereof, wherein the specimens are disposed in side-by-side relationship and are simultaneously subjected to longitudinal pulling stresses, said tensile strength testing system comprising, in combination, area scanning means for translating the optical characteristics of at least all the specimens into an electrical signal, said area scanning means comprising means to produce the electrical signal repeatedly with the progress of the tensile testing of the specimens, and circuit means for deriving from the output signal of said area scanning means sets of data representative of the varying lengths of the test regions of the respective specimens.

16. A tensile strength testing system as claimed in claim 15, wherein said circuit means comprises a plurality of gate means supplied with the output signal of said area scanning means, and a plurality of transverse boundary signal generator means for establishing transverse boundaries of the respective specimens, said transverse boundary signal generator means comprising means to supply to the respective gate means gating signals each representing a time when one of the specimens is being scanned, whereby said gate means produce outputs corresponding to the respective specimens.

17. A tensile strength testing system as claimed in claim 16, wherein the system includes reference signal generator means for driving said area scanning means, and wherein said transverse boundary signal generator means comprises means to produce the gating signals by utilizing a reference signal generated by said reference signal generator means.

18. A tensile strength system as claimed in claim 16, wherein said circuit means further comprises longitudinal boundary signal generator means for establishing longitudinal boundaries common to all the specimens, said longitudinal boundary signal generator means comprises means to supply to said gate means a common gating signal representing the time what at least the test regions of the specimens are being scanned, whereby said gate means derive from the output signal of said area scanning means its portions corresponding to the test regions of the respective specimens.

19. A tensile strength testing system as claimed in claim 18, wherein the specimens are gripped each at both ends by movable and fixed specimen gripping means, wherein the system includes at least one boundary member movable with said movable specimen gripping means, said boundary member having a predetermined optical characteristic and being scanned by said area scanning means along with the specimens, and wherein said longitudinal boundary signal generator means comprises means to produce the gating signal by utilizing those portions of the output signal of said area scanning means which correspond to said boundary member.

20. A tensile strength testing system as claimed in claim 18, wherein said longitudinal boundary signal generator means comprises means to produce the gating signal on the basis of time elapsed after the start of the tensile testing of the specimens.

21. A tensile strength testing system as recited in claim 18, wherein the system includes reference signal generator means for driving said area scanning means, and wherein said longitudinal boundary signal generator means comprises means to produce the gating signal by utilizing output from said reference signal generator means and those portions of the output signal of said area scanning means which correspond to the test regions of the specimens.

22. A tensile strength testing system for use with a specimen having a test region defined thereon by at least one marking having a different optical characteristic from the other surfaces of the specimen, wherein the specimen is adapted to be subjected to increasing longitudinal pulling stress, said tensile testing system comprising, in combination, a reference length surface of a prescribed optical characteristic disposed in the vicinity of the specimen being tested, said reference length surface being adapted to provide a predetermined reference length in the longitudinal direction of the specimen, area scanning means for translating the optical characteristics of at least the specimen and said reference length surface into an electrical signal, said area scanning means comprising means to produce the electrical signal repeatedly with the progress of the tensile testing of the specimen, first circuit means for deriving from the output signal of said area scanning means its portions representative of the varying length of the test region of the specimen, and second circuit means for deriving from the output signal of said area scanning means its portions representative of the reference length provided by said reference length surface.

23. A tensile strength testing system as claimed in claim 22, further comprising load detector means for generating an electrical signal representative of the pulling stress exerted on the specimen, rupture detector means for generating an electrical signal upon rupture of the specimen, and arithmetic means supplied with the output signals of said first and said second circuit means and said load detector means and said rupture detector means for computing desired stress-strain properties of the specimen.

24. A tensile strength testing system as claimed in claim 23, wherein said arithmetic means comprises means to compute the length of the test region of the specimen from the output signals of said first and said second circuit means.

25. A tensile testing system for opto-electronically indicating the stress-strain properties of materials under tension comprising, in combination, scanning means for scanning an elongated test specimen made of a material being tensile tested and a test region of the test specimen subjected to elongation by pulling stresses during tensile testing and for detecting and converting to an electrical output signal an optical characteristic of the test region different from other optical characteristics of other surfaces of the test specimen and developing said output signal as elongation of the test region progresses, circuit means receptive of said output signal for deriving portions representative of the increasing length of said test region, said scanning means comprising a line scanner to scan the test specimen along a line extending in a longitudinal direction thereof, and means for confirming that said scanner precisely scans said test specimen along said line.

* * * * *